US008143412B2

(12) United States Patent
Priebe et al.

(10) Patent No.: US 8,143,412 B2
(45) Date of Patent: Mar. 27, 2012

(54) INHIBITORS OF PROLIFERATION AND ACTIVATION OF SIGNAL TRANSDUCER AND ACTIVATOR OF TRANSCRIPTION (STATS)

(75) Inventors: Waldemar Priebe, Houston, TX (US); Stanislaw Skora, Houston, TX (US); Timothy Madden, Sugar Land, TX (US); Izabela Fokt, Houston, TX (US); Charles Conrad, Spring, TX (US)

(73) Assignee: Board of Regents, The University of Texas System

( * ) Notice: Subject to any disclaimer, the term of this patent is extended or adjusted under 35 U.S.C. 154(b) by 0 days.

(21) Appl. No.: 12/989,944

(22) PCT Filed: Jun. 26, 2009

(86) PCT No.: PCT/US2009/048782
§ 371 (c)(1),
(2), (4) Date: Oct. 27, 2010

(87) PCT Pub. No.: WO2010/005807
PCT Pub. Date: Jan. 14, 2010

(65) Prior Publication Data
US 2011/0053992 A1 Mar. 3, 2011

Related U.S. Application Data

(60) Provisional application No. 61/079,002, filed on Jul. 8, 2008.

(51) Int. Cl.
*C07D 213/57* (2006.01)
*A61K 31/44* (2006.01)
(52) U.S. Cl. ........................ 546/330; 514/357
(58) Field of Classification Search ........................ None
See application file for complete search history.

(56) References Cited

U.S. PATENT DOCUMENTS

| 7,745,468 | B2 | 6/2010 | Priebe et al. |
| 7,807,719 | B2 | 10/2010 | Roifman et al. |
| 2005/0277680 | A1 | 12/2005 | Priebe et al. |
| 2006/0058297 | A1 | 3/2006 | Roifman et al. |
| 2007/0232668 | A1 | 10/2007 | Priebe et al. |
| 2008/0167277 | A1 | 7/2008 | Conrad et al. |
| 2009/0163545 | A1 | 6/2009 | Goldfarb |
| 2010/0152143 | A1 | 6/2010 | Priebe et al. |

FOREIGN PATENT DOCUMENTS

| DE | 1212984 B | 3/1966 |
| DE | 4330105 A1 | 3/1993 |
| JP | 41-3540 | 3/1966 |
| JP | 41003540 B4 | 3/1966 |
| WO | WO9905109 A1 | 2/1999 |
| WO | W/03073999 A2 | 9/2003 |
| WO | WO03086396 A1 | 10/2003 |
| WO | WO2005000777 | 1/2005 |
| WO | WO2005058829 A1 | 6/2005 |
| WO | WO2005092904 | 10/2005 |
| WO | WO2006029515 A1 | 3/2006 |
| WO | 2006057824 A2 | 6/2006 |
| WO | WO2006005782 A2 | 6/2006 |
| WO | WO2006086422 A2 | 8/2006 |
| WO | WO2007006143 | 1/2007 |
| WO | WO2007115269 A2 | 10/2007 |
| WO | WO2007130523 A2 | 11/2007 |
| WO | WO2008005954 | 1/2008 |
| WO | WO2008005954 A2 | 1/2008 |
| WO | WO2008000794 A2 | 3/2008 |
| WO | 2008079460 A2 | 7/2008 |
| WO | 2008083389 A1 | 7/2008 |
| WO | WO2008118445 A1 | 10/2008 |
| WO | WO2008121858 A1 | 10/2008 |
| WO | WO2009073575 A2 | 6/2009 |
| WO | 2009091506 A2 | 7/2009 |
| WO | WO2009009150 A2 | 7/2009 |
| WO | WO2010081158 A2 | 7/2010 |

OTHER PUBLICATIONS

Silverman, R., "The Organic Chemistry of Drug Design and Drug Action," 2004, Elsevier, pp. 29-32.*
International Preliminary Report on Patentability dated Jan. 20, 2011.
Horiguchi, A. et al., STAT3 Inhibitor WP1066 As a Novel Therapeutic Agent for Renal Cell Carcinoma, British Journal of Cancer,102(11), 1592-1599CODEN: BJCAAI;ISSN: 0007-0920. (2010).
Kupferman, Michael, E. et al., Therapeutic Suppression of Constitutive and Inducible JAK\STAT Activation in Head and Neck Squamous Cell Carcinoma, Journal of Experimental Therapeutics and Oncology, 8(2), 117-127 CODEN: JETOFX; ISSN: 1359-4117 (2009).
Kong, Ling-Yuan, et al., A Novel Phosphorylated STAT3 Inhibitor Enhances T Cell Cytotoxicity Against Melanoma Through Inhibition of Regulatory T Cells , Cancer Immunology Immunotherapy, 58(7), 1023-1032 CODEN:CIIMDN; ISSN: 0340-7004 (2009).
Kong, Ling-Yuan, et al., A Novel Inhibitor of Signal Transducers and Activators of Transcription 3 Activation Is Efficacious Against Established Central Nervous System Melanoma and Inhibits Regulatory T Cells, Clinical Cancer Research, 14(18), 5759-5768 CODEN: CCREF4; ISSN: 1078-0432(2008). Verstovsek, Srdan, et al., WP1066, a Novel JAK2 Inhibitor, Suppresses Proliferation and Induces Apoptosis in Erythroid Human Cells Carrying the JAK2 V617F Mutation Clinical Cancer Research (2008), 14(3), 788-796 CODEN: CCREF4; ISSN: 1078-0432(2008).
Ferrajoli, Alessandra, et al., WP1066 Disrupts Janus Kinase-2 and Induces Caspase-Dependent Apoptosis in Acute Myelogenous Leukemia Cells, Cancer Research, 67(23), 11291-11299 CODEN: CNREA8; ISSN: 0008-5472(2007).
Hussain, S. Farzana, et al., A Novel Small Molecule Inhibitor of Signal Transducers and Activators of Transcription 3 Reverses Immune Tolerance in Malignant Glioma Patients, Cancer Research, 67(20), 9630- 9636 CODEN: CNREA8; ISSN: 0008-5472 (2007).
Bartholomeusz, Geoffrey, et al., Degrasyn Activates Proteasomal-Dependent Degradation of c-Myc, Cancer Research, 67(8), 3912-3918 CODEN: CNREA8; ISSN: 0008-5472 (2007).

(Continued)

*Primary Examiner* — Janet Andres
*Assistant Examiner* — Heidi Reese
(74) *Attorney, Agent, or Firm* — Nielsen IP Law LLC

(57) ABSTRACT

Pyridine compounds effective in modulation STAT3 and/or STAT5 activation are provided that are useful in the prevention and treatment of proliferative disease and conditions including cancer, inflammation and proliferative skin disorders.

9 Claims, 3 Drawing Sheets

OTHER PUBLICATIONS

Iwamaru, A., et al., A Novel Inhibitor of the STAT3 Pathway Induces Apoptosis in Malignant Glioma Cells Both in Vitro and in Vivo, Oncogene, 26(17), 2435-2444 CODEN: ONCNES; ISSN: 0950-9232(2007).

Schepetkin, Igor A., et al., Novel Small-Molecule Inhibitors of Anthrax Lethal Factor Identified by High-Throughput Screening, Journal of Medicinal Chemistry, 49(17), 5232-5244 CODEN: JMCMAR; ISSN: 0022-2623 (2006).

Duque, J., et al., Structure of N-benzyl-[2-cyano-3-(2'-furyl)acrylamide], Revista CENIC, Ciencias Quimicas, 27(1-2-3), 25-29 CODEN: RCCQER; ISSN: 1015-8553 (1996).

Hernandez, Ramon, et al., 2-Cyano-N-furfuryl-3-(2-furyl)acrylamide, Acta Crystallographica, Section C: Crystal Structure Communications, C52(1), 203-5 CODEN: ACSCEE; ISSN: 0108-2701 (1996).

Pomes, R., et al., Structure of N-(2-furfuryl)-2-cyano-3-(5-nitro-2-furyl)acrylamide, Anales de la Asociacion Quimica Argentina, 82(4), 249-55 CODEN: AAQAAE; ISSN: 0365-0375 (1994).

Durruthy, O., et al., Structure of N-(2-furylmethyl)-alpha-cyano-2-furanacrylamide, Acta Crystallographica, Section C: Crystal Structure Communications, C49(3), 558-9 CODEN: ACSCEE; ISSN: 0108-2701(1993).

Saikachi, Haruo, et al., Synthesis of furan derivatives. XVIII. 2-Cyano-3(5-nitro-2-furyl)acrylamides and esters, Chem. & Pharm. Bull. (Tokyo), 7, 453-6 (1959).

Darnell, J.E. jr. , Validating Stat3 in Cancer Therapy, Nature Medicine, 595-596, vol. 11, No. 6, Jun. 2005.

Heinrich, P.C., et al., Interleukin-6-Type Cytokine Signalling Through the GP130/Jak/STAT Pathway1 , Biochem ,J. 334, 297-314, (1998).

Seidel. H. M., et al., Pharmaceutical Intervention in the JAK/STAT Signaling Pathway, Oncogene, 19, 2645-2656, (2000).

Liu, H., et al., Immunohistochemical Localization of Activated Stat3 and hTERT Protein in Psoriasis Vulgaris, Eur J Dermatol , 16(2): 205-6, (2006).

Trajkovski, T., STAT3-A Promising Molecular Target for Cancer Therapy, University of Toronto Medical Journal, 16, vol. 83 2005 p. 16.

Pardanani, A., JAK2 Inhibitor Therapy in Myeloproliferative Disorders : Rationale, Preclinical Studies ans Ongoing Clinical Trials, Leukemia , 22, 23-30, (2008).

Yu, Hua, et al., The Stats of Cancer—New Molecular Targets Come of Age, Naure Reviews, vol. 4, 97-104, Feb. 2004.

Tefferi, A., et al., JAK2 in Myeloproliferative Disorders is Not Just Another Kinase, Cell Cycle, 4:8, 1053-1056, Aug. 2005.

Levy, D.E., et al., What Does Stat3 Do? The Journal of Clinical Investigation, vol. 109, No. 9, May 2002.

Nikitakis, N. G., et al., Targeting the STAT Pathway in Head and Neck Cancer: Recent Advances and Future Prospects, Current Cancer Drug Targets, 4, 637-651, (2004).

Sun, J., et al., Cucurbitacin Q: A Selective STAT3 Activation Inhibitor with Potent Antitumor Activity, Oncogene 24, 3236-3245 (2005).

Rahaman, S.O., et al., Inhibition of Constitutively Active Stat3 Suppresses Proliferation and Induces Apoptosis in Glioblastoma Multiforme Cells, Oncogene, 21, 8404-8413, (2002).

Xie, T., et al., Stat3 Activation Regulates the Expression of Matrix Metalloproteinase-2 and Tumor Invasion and Metastasis, Oncogene , 23, 3550-3560, (2004).

Huang, S., Regulation of Metastases by Signal Transducer and Activator of Transcription 3 Signaling Pathway: Clinical Implications, Clin Cancer Res 2007, 13(5) 1362-1366, Mar. 1, 2007.

Xie, T., et al., Activation of Stat3 in Human Melanoma Promotes Brain Metastasis, Cancer Res 2006, 66:(6), 3188-3196, Mar. 15, 2006.

Levy, D.E., et al., STAT3: A Multifacted Oncogene ,PNAS, vol. 103, No. 27, 10151-10152, Jul. 5, 2006.

Kisseleva, T., et al., Signaling Through the JAK/STAT Pathway, Recent Advances and Future Challenges, Gene 285: 1-24 (2002).

Chen, X., et al., Crystal Structure of a Tyrosine Phosphorylated STAT-1 Dimer Bound to DNA, Cell 93: 827-839 (1998).

Song, J.I., et al., STAT Signaling in Head and Neck Cancer, Oncogene, 19: 2489-2495, (2000).

Kijima, T. et al., STAT3 Activation Abrogates Growth Factor Dependence and Contributes to Head and Neck Squamous Cell Carcinoma Tumor Growth in Vivo, Cell Growth Differ, 13: 355-362, (2002).

Song, L. et al., Activation of Stat3 by Receptor Tyrosine Kinases and Cytokines Regulates Survival in Human Non-Small Cell Carcinoma Cells, Oncogene, 22: 4150-4165, (2003).

Gadina, M., et al., Signaling by Type I and Type II Cytokine Receptors: Ten Years After, Curr. Opin. Immunol. 13:363, (2001).

Horvath, C.M. The Jak-STAT Pathway Stimulated by Interferon Gamma, Science, STKE, 260:tr8, (2004).

Lai, S.Y., et al., Erythropoietin-Mediated Activation of JAK-STAT Signaling Contributes to Cellular Invasion in Head and Neck Squamous Cell Carcinoma, Oncogene, 24: 4442-4449, (2005).

Siavash, H., et al., Abrogation of IL-6-Mediated JAK Signalling by the Cyclopentenone Prostaglandin 15d-PGJ(2) in Oral Squamous Carcinoma Cells, Br J Cancer, 91: 1074-1080, (2004).

Quadros, M.R., et al., Complex Regulation of Signal Transducers and Activators of Transcription 3 Activation in Normal and Malignant Keratinocytes, Cancer Res, 64 :3934-3939,(2004).

Hebenstreit D. et al., JAK/STAT-Dependent Gene Regulation by Cytokines, Drug News Perspect. vol. 18 (4), pp. 243-249(2005).

Boulton, TG, Zhong, Z, Wen, Z, Darnell, Jr, JE, Stahl, N, and Yancopoulos, GD, STAT3 Activation by Cytokines Utilizing gp130 and Related Transducers Involves a Secondary Modification Requiring an H7-Sensitive Kinase Proc Natl Acad Sci U S A. 92(15): 6915-6919 (1995).

Yuan ZL et al., Central Role of the Threonine Residue within the p_1 Loop of Receptor Tyrosine Kinase in STAT3 Constitutive Phosphorylation in Metastatic Cancer Cells Mol. Cell Biol. vol. 24 (21), pp. 9390-9400. (2004).

Silva C.M. Role of Stats as Downstream Signal Transducers in Src Family Kinase-Mediated Tumorigenesis Oncogene vol. 23 (48), pp. 8017-8023. (2004).

O'shea, J. J.et al., A New Modality for Immunosuppression: Targeting the JAK/STAT Pathway, Nature Rev. Drug Disc. (3): 555-564(2004).

Hellgren, G.,et al., The Growth Hormone Receptor Associates with Jak1, Jak2 and Tyk2 in Human Liver, Growth Horm. IGF Res. 9(3):212-8 (1999).

Krebs, L. et al. SOCS Proteins: Negative Regulators of Cytokine Signaling Stem Cells vol. 19, pp. 378-387 (2001).

Shuai, K Regulation of Cytokine Signaling Pathways by PIAS Proteins vol. 16 (2), pp. 196-202. (2006).

Leaman, D. W. et al., Roles of JAKs in Activation of STATs and Stimulation of c-fos Gene Expression by Epidermal Growth Factor, Mol Cell Biol. 16(1): 369-375(1996).

* cited by examiner

INHIBITORS OF PROLIFERATION AND ACTIVATION OF SIGNAL TRANSDUCER AND ACTIVATOR OF TRANSCRIPTION (STATS)

CROSS-REFERENCE TO RELATED APPLICATIONS

This application claims priority to U.S. Provisional Application Ser. No. 61/079,002 filed on Jul. 8, 2008. The application is incorporated by reference herein in its entirety.

STATEMENT REGARDING FEDERALLY SPONSORED RESEARCH OR DEVELOPMENT

None.

THE NAMES OF THE PARTIES TO A JOINT RESEARCH AGREEMENT

None.

REFERENCE TO SEQUENCE LISTING

None.

FIELD OF THE INVENTION

Pyridine compounds and compositions and their application as pharmaceuticals for the treatment of disease are provided herein. Methods of inhibiting of STAT3 and/or STAT5 activation in a human or animal subject are also provided for the treatment of diseases such as cancer.

BACKGROUND OF THE INVENTION

The Jak/STAT signaling pathway is known to be activated in a number of cancers and inflammatory diseases. When activated through phosphorylation of a single tyrosine residue STAT3 dimerizes, translocates to nucleus, and serves as a transcription factor driving the upregulation of a number of proliferative and pro-survival genes including survivin, VEGF, Bcl-2, and Bcl-xL. These gene products are known to promote the growth and metastasis of over 20 tumor types and are also associated with the promotion of several proliferative skin disorders including psoriasis, T-cell lymphoma, and atopic dermatitis.

Inhibition of STAT3 phosphorylation in tumor bearing animals leads to the induction of apoptotic cell death and in preclinical orthotopic models of several diseases a significant reduction in tumor size. Likewise in inflammatory skin diseases inhibition of STAT3 phosphorylation leads to resolution of plaques, scales, and other associated lesions.

While the development of inhibitors of this pathway is currently desirable, a variety of inhibition (such as small molecule, antisense, iRNA) approaches have been tried with unsatisfactory results.

SUMMARY OF THE INVENTION

Novel pyridine compounds and pharmaceutical compositions that inhibit cancer, have been found, together with methods of synthesizing and using the compounds including methods for the treatment of STAT3-mediated diseases and conditions in a patient by administering the compounds. The compounds can also be useful in treating STAT5-mediated diseases and conditions. This class of compounds is defined by structural Formula I as follows:

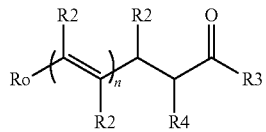

or a pharmaceutically acceptable salt or solvate thereof, wherein:

n is an integer selected from 1, 2 or 3;

$R_0$ is $R_1$, or $R_o$ is $R_1—Z_1—$ wherein $Z_1$ is alkyl, and specifically may be a lower alkyl such as $—(CH_2)_{m3}-$ where $m_3=0, 1, 2, 3,$ or $4$;

$R_1$ is:

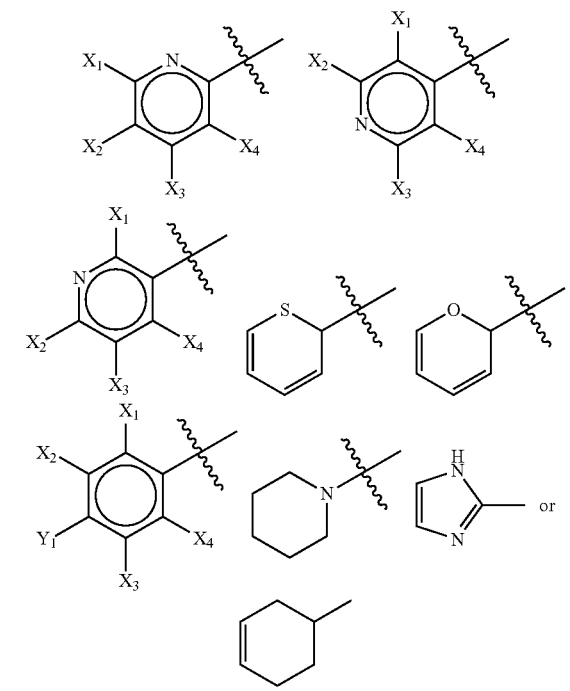

wherein $X_1, X_2, X_3,$ and $X_4,$ are each independently hydrogen, halogen, alkyl, alkoxy, OH, trihalomethyl, or $NO_2$, and $Y_1$ is OH, halogen, specifically including Br and Cl, or $O_2N$;

$R_2$ is alkyl, alkenyl, alkynyl, alkoxy, alkylaryl, halogen, hydrogen, OH, $NO_2$, thioether, amine, SH, or $NH_2$;

$R_3$ is:

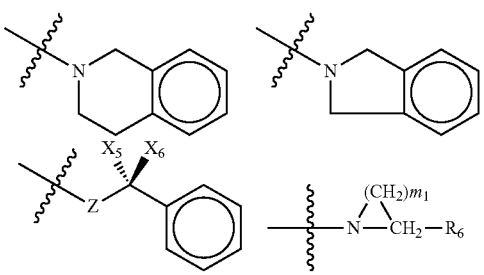

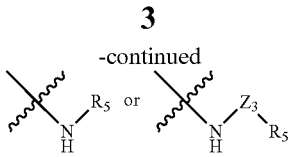

wherein $m_1$ is an integer selected from 1, 2, 3, or 4, $X_5$ and $X_6$ are each independently hydrogen, alkyl, upper alkyl, lower alkyl, aryl, alkoxyl, aryloxyl, cyclic alkyl, cycloalkyl, cycloarylalkyl, aralkyl, alkylester, alkylesteralkyl, alkylacetoxyl, hydroxyl, hydroxylalkyl, cyclopropyl, cyclobutyl, —$CH_3$, —$CH_2OH$, cyclopentyl, —$CH_2OAc$, —$CH_2OC(O)C(CH_3)_3$, —$CH_2C_6H_5$, or cyclohexyl, Z is NH, S, or O, and $Z_3$ is alkyl or lower alkyl;

$R_4$ is CN, substituted amine, $CH_2S$-alkyl, alkyl, or $CH_2N_3$; and $R_5$ and $R_6$ are each independently selected from the group consisting of:

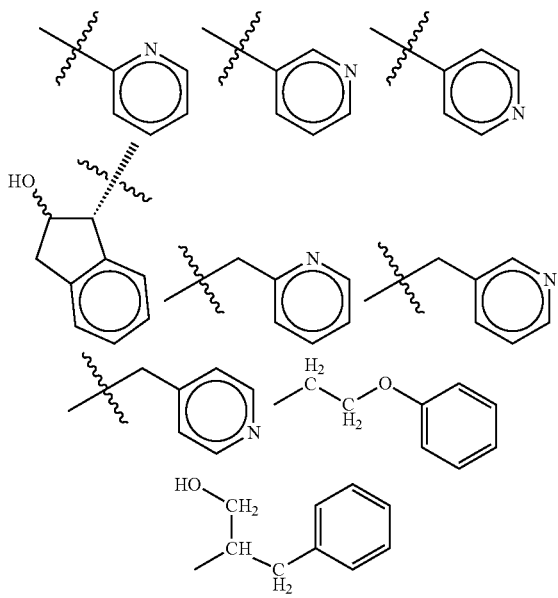

monosaccharide (e.g., glucose, fructose, galactose, etc.), polysaccharide, monosaccharide derivative (e.g., an acetylated monosaccharide such as acetylated galactose, 1,2,3,4-diisopropylideno-D-g-alactose) substituted and unsubstituted aryl, and substituted and unsubstituted alkylaryl.

The compounds described herein possess useful STAT3 inhibiting activity, and may be used in the treatment or prophylaxis of a disease or condition in which STAT3 plays an active role. Thus, in broad aspect, pharmaceutical compositions comprising one or more compounds of the present invention together with a pharmaceutically acceptable carrier, as well as methods of making and using the compounds and compositions is described.

Methods for inhibiting STAT3 or STAT5 activation are also provided herein. Methods for treating a STAT3-mediated or STAT5-mediated disorder in a patient in need of such treatment comprising administering to said patient a therapeutically effective amount of a compound or composition described herein. Further, these compounds presented herein can be used in the manufacture of a medicament for the treatment of a disease or condition ameliorated by the modulation of STAT3 or STAT5 activation.

BRIEF DESCRIPTION OF THE DRAWINGS

The foregoing summary as well as the following detailed description of the preferred embodiment of the invention will be better understood when read in conjunction with the appended drawings. It should be understood, however, that the invention is not limited to the precise arrangements and instrumentalities shown herein.

For a more complete understanding of the present invention, and the advantages thereof, reference is now made to the following descriptions taken in conjunction with the accompanying drawings, in which.

DETAILED DESCRIPTION

Figure 1:
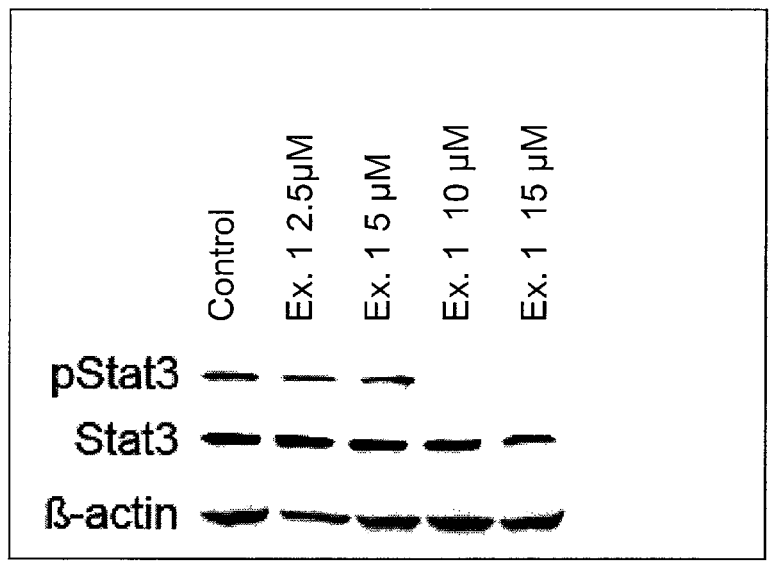
FIG. 1 is data from experimentation that shows the inhibition of STAT3 phosphorylation by the compound of Example 1 in Colo357FG tumor cell line.
Figure 2:
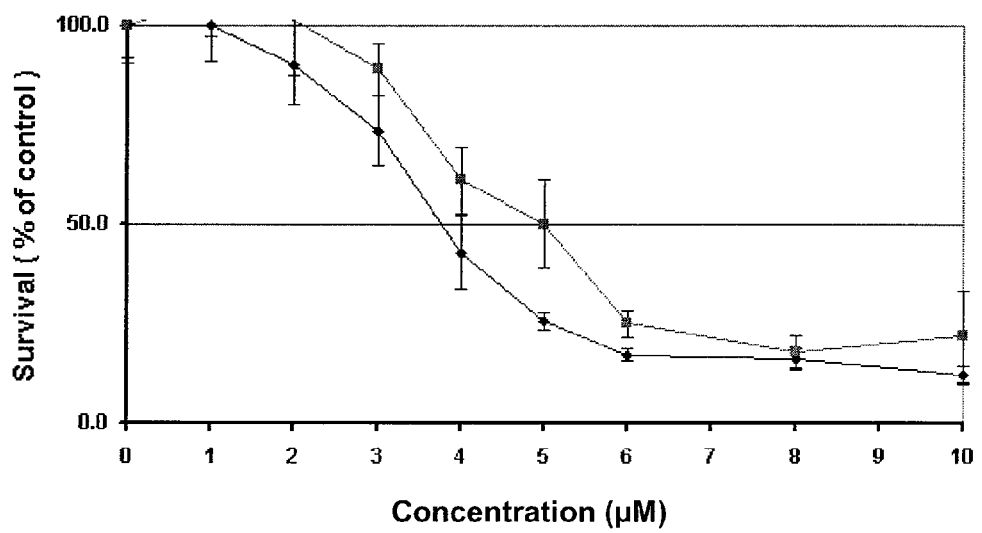
FIG. 2 provides a chart of the data show the lack of cell survival of the U87 brain tumor after administration of the compounds of Example 2 and Example 4.
Figure 3:
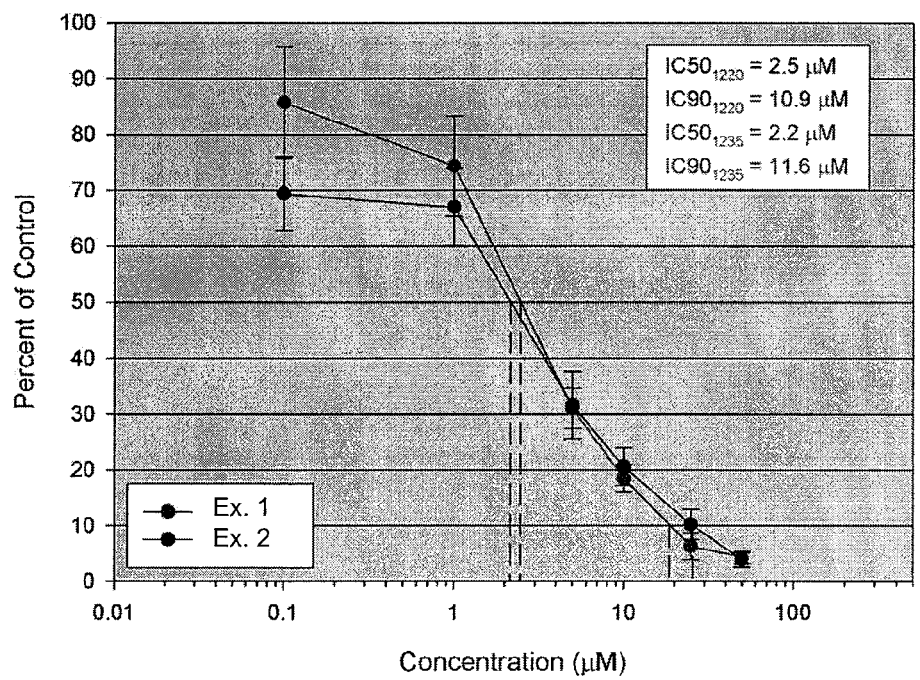
FIG. 3 depicts the data depicting the inhibition of the SCOVE3 ovarian cancer cell growth after administration of the compounds of Example 2 and Example 4.
Figure 4:
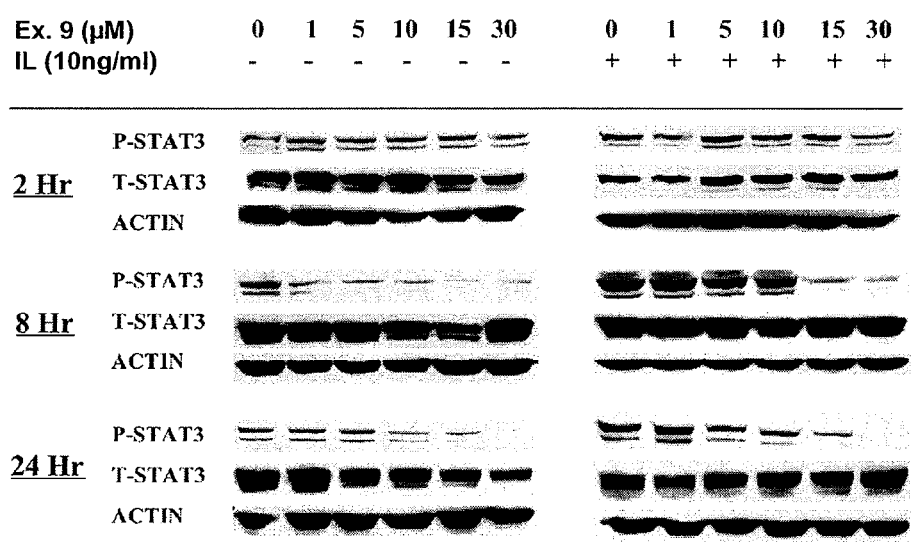
FIG. 4 is data from the compound of Example 9 constitutively inhibiting the IL-2 phosphorylation of STAT-3 in D54 brain tumor cell lines.

Compounds presented herein have the general Formula I:

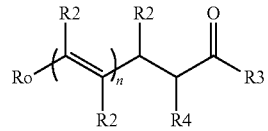

or a pharmaceutically acceptable salt or solvate thereof, wherein:

n is an integer selected from 1, 2 or 3;

$R_O$ is $R_1$, or $R_o$ is $R_1$—$Z_1$— wherein $Z_1$ is alkyl, and specifically may be a lower alkyl such as —$(CH_2)_{m3}$- where $m_3$=0, 1, 2, 3, or 4;

$R_1$ is:

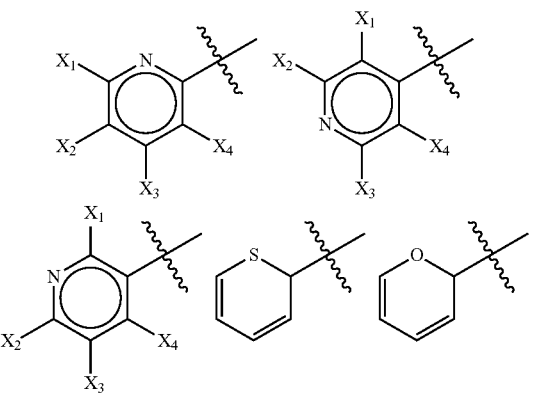

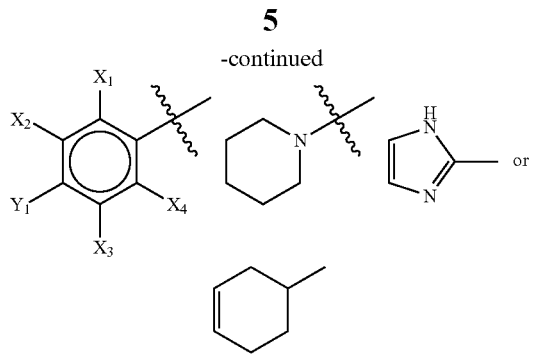

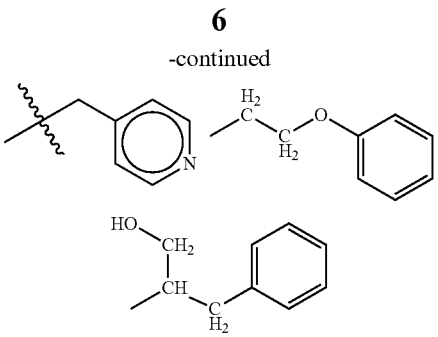

wherein $X_1$, $X_2$, $X_3$, and $X_4$, are each independently hydrogen, halogen, alkyl, alkoxy, OH, trihalomethyl, or $NO_2$, and $Y_1$ is OH, halogen, specifically including Br and Cl, or $O_2N$;

$R_2$ is alkyl, alkenyl, alkynyl, alkoxy, alkylaryl, halogen, hydrogen, OH, $NO_2$, thioether, amine, SH, or $NH_2$;

$R_3$ is:

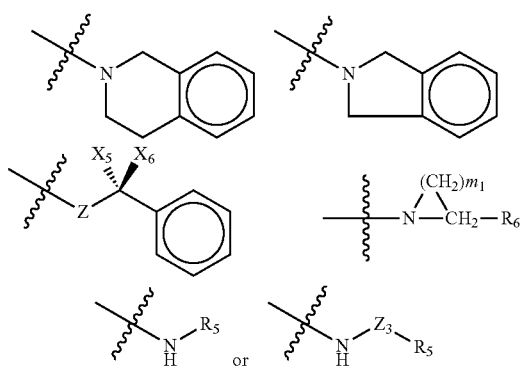

wherein $m_1$ is an integer selected from 1, 2, 3, or 4, $X_5$ and $X_6$ are each independently hydrogen, alkyl, upper alkyl, lower alkyl, aryl, alkoxyl, aryloxyl, cyclic alkyl, cycloalkyl, cycloarylalkyl, aralkyl, alkylester, alkylester-alkyl, alkylacetoxyl, hydroxyl, hydroxylalkyl, cyclopropyl, cyclobutyl, —$CH_3$, —$CH_2OH$, cyclopentyl, —$CH_2OAc$, —$CH_2OC(O)C(CH_3)_3$, —$CH_2C_6H_5$, or cyclohexyl, Z is NH, S, or O, and $Z_3$ is alkyl or lower alkyl;

$R_4$ is CN, substituted amine, $CH_2S$-alkyl, alkyl, or $CH_2N_3$; and $R_5$ and $R_6$ are each independently selected from the group consisting of:

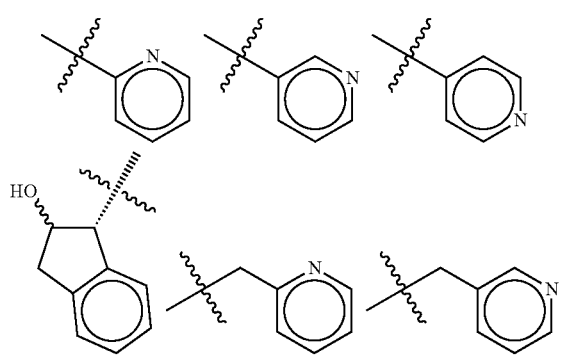

monosaccharide (e.g., glucose, fructose, galactose, etc.), polysaccharide, monosaccharide derivative (e.g., an acetylated monosaccharide such as acetylated galactose, 1,2,3,4-diisopropylideno-D-g-alactose) substituted and unsubstituted aryl, and substituted and unsubstituted alkylaryl.

More specifically, $R_5$ may be an alkylaryl having the structure:

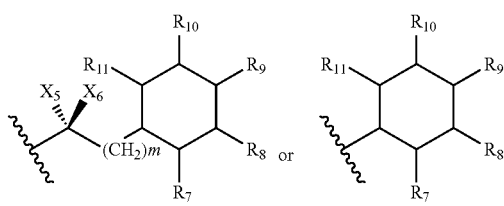

wherein m is an integer selected from 0, 1, 2, 3, 4, 5, 6, or 7, $X_5$ and $X_6$ are each independently hydrogen, alkyl, upper alkyl, lower alkyl, aryl, alkoxyl, aryloxyl, cyclic alkyl, cycloalkyl, cycloarylalkyl, aralkyl, alkylester, alkylester-alkyl, alkylacetoxyl, hydroxyl, hydroxylalkyl, cyclopropyl, cyclobutyl, —$CH_3$, —$CH_2OH$, cyclopentyl, —$CH_2OAc$, —$CH_2OC(O)C(CH_3)_3$, —$CH_2C_6H_5$, or cyclohexyl, and $R_7$, $R_8$, $R_9$, $R_{10}$, and $R_{11}$, are each independently selected from the group consisting of hydrogen, halogen, alkyl, alkoxy, OH, trihalomethyl, and $NO_2$.

Even more specifically, $R_5$ can be any one of the following:

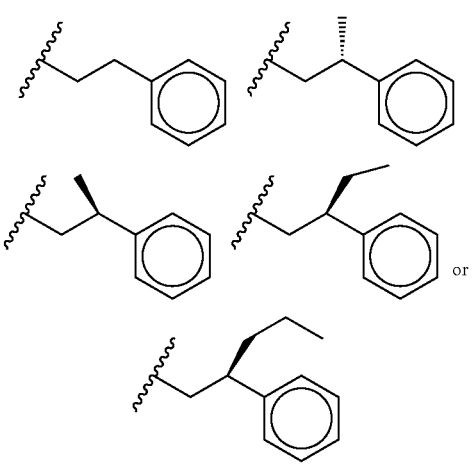

Furthermore, in Formula I, $R_1$ may be specifically:

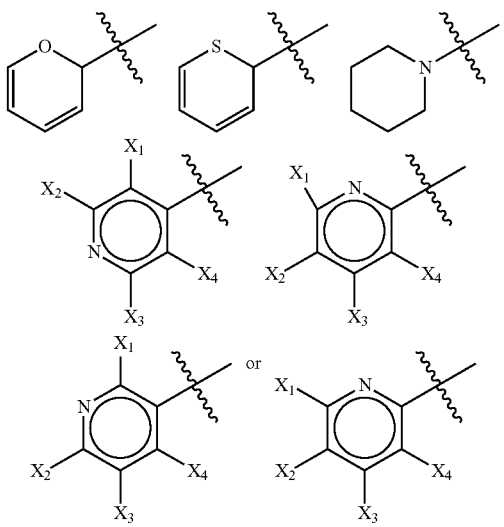

wherein $X_1$ may be a halogen such as Br or Cl, and $X_2$, $X_3$, and $X_4$, are each independently hydrogen, halogen, alkyl, alkoxy, OH, trihalomethyl, or $NO_2$.

As used herein, the terms below have the meanings indicated.

As used herein, the term "amino" means $-NH_2$; the term "nitro" means $-NO_2$; the term "halo" designates $-F$, $-Cl$, $-Br$ or $-I$; the term "mercapto" means $-SH$; the term "cyano" means $-CN$; the term "silyl" means $-SiH_3$, and the term "hydroxy" means $-OH$.

An "amide" refers to a $-C(O)-NH-R$, where R is either alkyl, aryl, alkylaryl, or hydrogen.

A "thioamide" refers to a $-C(S)-NH-R$, where R is either alkyl, aryl, alkylaryl, or hydrogen.

An "ester" refers to a $-C(O)-OR'$, where R' is either alkyl, aryl, or alkylaryl.

An "amine" refers to a $-N(R'')R'''$, where R'' and R''' is each independently either hydrogen, alkyl, aryl, or alkylaryl, provided that R'' and R''' are not both hydrogen.

A "thioether" refers to $-S-R$, where R is either alkyl, aryl, or alkylaryl.

A "sulfonyl" refers to $-S(O)_2-R$, where R is aryl, $C(CN)=C$-aryl, $CH_2-CN$, alkylaryl, NH-alkyl, NH-alkylaryl, or NH-aryl.

An "alkane" refers to an acyclic branched or unbranched hydrocarbon, in many cases having the general formula $C_nH_{2n+2}$.

An "alkyl" refers to a univalent group derived from an alkane by removal of a hydrogen atom from any carbon atom thus having the formula $-C_nH_{2n+1}$ in many cases. Alkyl groups include either straight-chained or branched chained and/or groups that may be substituted with additional acyclic alkyl, cycloalkyl, or cyclic alkyl groups. An alkyl group may be heteroatom-substituted or heteroatom-unsubstituted, see below. Preferably, an alkyl group has 1 to 12 carbons and may be referred to as a lower alkyl when having 1 to 7 carbons, and/or an upper alkyl when having 8 or more carbon atoms. Alkyl further refers and includes a "divalent alkyl" that refers to a divalent group derived from an alkane by removal of two hydrogen atoms from either the same carbon atom (e.g. methylene, ethylidene, propylidene) or from different carbon atoms (e.g. $-C_2H_4-$).

A "cycloalkane" refers to saturated monocyclic hydrocarbons with or without side chains.

A "cycloalkyl" specifically refers to a univalent group derived from cycloalkane by removal of a hydrogen atom from a ring carbon atom.

A cyclic alkyl and/or alkyl cyclic or alicyclic compound refers to an aliphatic compound having a carbocyclic ring structure that may be saturated or unsaturated, but are not a benzenzoid or other aromatic system, and where the univalent group is derived by removal of a hydrogen atom from any carbon of alkane chain.

The term "heteroatom-substituted," when used to modify a class of organic radicals (e.g. alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, $=O$, $=S$, $-NO_2$, $-N(CH_3)_2$, amino, or $-SH$. Specific heteroatom-substituted organic radicals are defined more fully below.

The term "heteroatom-unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group $-C_6H_4C\equiv CH$ is an example of a heteroatom-unsubstituted aryl group, while $-C_6H_4F$ is an example of a heteroatom-substituted aryl group. Specific heteroatom-unsubstituted organic radicals are defined more fully below.

The term "heteroatom-unsubstituted $C_n$-alkyl" refers to an alkyl, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, $-CH_3$, cyclopropylmethyl, $-CH_2CH_3$, $-CH_2CH_2CH_3$, $-CH(CH_3)_2$, $-CH_2CH_2CH_2CH_3$, $-CH(CH_3)CH_2CH_3$, $-CH_2CH(CH_3)_2$, $-C(CH_3)_3$, and $-CH_2C(CH_3)_3$ are all examples of heteroatom-unsubstituted alkyl groups.

The term "heteroatom-substituted $C_n$-alkyl" refers to an alkyl, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all examples of heteroatom-substituted alkyl groups: trifluoromethyl, $-CH_2F$, $-CH_2Cl$, $-CH_2Br$, $-CH_2OH$, $-CH_2OCH_3$, $-CH_2OCH_2CH_3$, $-CH_2OCH_2CH_2CH_3$, $-CH_2OCH(CH_3)_2$, $-CH_2OCH_2CF_3$, $-CH_2OCOCH_3$, $-CH_2NH_2$, $-CH_2NHCH_3$, $-CH_2N(CH_3)_2$, $-CH_2NHCH_2CH_3$, $-CH_2N(CH_3)CH_2CH_3$, $-CH_2NHCH_2CH_2CH_3$, $-CH_2NHCH(CH_3)_2$, $-CH_2OCH(CH_2)_2$, $-CH_2NHCH(CH_2)_2$, $-CH_2CH_2NHCH(CH_2)_2$, $-CH_2N(CH_2CH_3)_2$, $-CH_2CH_2F$, $-CH_2CH_2Cl$, $-CH_2CH_2Br$, $-CH_2CH_2I$, $-CH_2CH_2OH$, $CH_2CH_2OCOCH_3$, $-CH_2CH_2NH_2$, $-CH_2CH_2N(CH_3)_2$, $-CH_2CH_2NHCH_2CH_3$, $-CH_2CH_2N(CH_3)CH_2CH_3$, $-CH_2CH_2NHCH_2CH_3$, $-CH_2CH_2NHCH(CH_3)_2$, $-CH_2CH_2N(CH_2CH_3)_2$, $-CH_2CH_2NHCO_2C(CH_3)_3$, and $-CH_2Si(CH_3)_3$.

The term "heteroatom-unsubstituted $C_n$-cycloalkyl" refers to a cycloalkyl, further having a total of n carbon atoms, all of which are nonaromatic, 3 or more hydrogen atoms, and no heteroatoms. For example, a heteroatom-unsubstituted $C_1$-$C_{10}$-cycloalkyl has 1 to 10 carbon atoms. The groups —CH(CH$_2$)$_2$ (cyclopropyl), cyclobutyl, cyclopentyl, and cyclohexyl, are all examples of heteroatom-unsubstituted cycloalkyl groups.

The term "heteroatom-substituted C$_n$-cycloalkyl" refers to a cycloalkyl, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted C$_1$-C$_{10}$-cycloalkyl has 1 to 10 carbon atoms.

An "alkenyl" group refers to an unsaturated hydrocarbon group containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted, the substituted group(s) is preferably hydroxyl, cyano, alkoxy, =O, =S, NO$_2$, N(CH$_3$)$_2$, halogen, amino, or SH.

The term "heteroatom-unsubstituted C$_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted C$_2$-C$_{10}$-alkenyl has 2 to 10 carbon atoms. Heteroatom-unsubstituted alkenyl groups include: —CH=CH$_2$, —CH=CHCH$_3$, —CH=CHCH$_2$CH$_3$, —CH=CHCH$_2$CH$_2$CH$_3$, —CH=CHCH(CH$_3$)$_2$, —CH=CHCH(CH$_2$)$_2$, —CH$_2$CH=CH$_2$, —CH$_2$CH=CHCH$_3$, —CH$_2$CH=CHCH$_2$CH$_3$, —CH$_2$CH=CHCH$_2$CH$_2$CH$_3$, —CH$_2$CH=CHCH(CH$_3$)$_2$, —CH$_2$CH=CHCH(CH$_2$)$_2$, and —CH=CH—C$_6$H$_5$.

The term "heteroatom-substituted C$_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted C$_2$-C$_{10}$-alkenyl has 2 to 10 carbon atoms. The groups, —CH=CHF, —CH=CHCl and —CH=CHBr, are examples of heteroatom-substituted alkenyl groups.

An "alkynyl" group refers to an unsaturated hydrocarbon group containing at least one carbon-carbon triple bond, including straight-chain, branched chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted, the substituted group(s) is preferably hydroxyl, cyano, alkoxy, =O, =S, NO$_2$, N(CH$_3$)$_2$, amino, or SH.

The term "heteroatom-unsubstituted C$_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted C$_2$-C$_{10}$-alkynyl has 2 to 10 carbon atoms. The groups, —C≡CH, —C≡CCH$_3$, and —C≡CC$_6$H$_5$ are examples of heteroatom-unsubstituted alkynyl groups.

The term "heteroatom-substituted C$_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted C$_2$-C$_{10}$-alkynyl has 2 to 10 carbon atoms. The group, —C≡CSi(CH$_3$)$_3$, is an example of a heteroatom-substituted alkynyl group.

An "aryl" group refers to an aromatic group which has at least one ring having a conjugated pi electron system, and includes carbocyclic aryl, heterocyclic aryl, and biaryl groups, all of which may be optionally substituted. Preferably, the aryl is a substituted or unsubstituted phenyl or pyridyl. Preferred aryl substituent(s) are halogen, trihalomethyl, hydroxyl, SH, OH, NO$_2$, amine, thioether, cyano, alkoxy, alkyl, and amino groups.

An "alkylaryl" group refers to an alkyl (as described above), covalently joined to an aryl group (as described above). Preferably, the alkyl is a lower alkyl.

"Carbocyclic aryl" groups are groups wherein the ring atoms on the aromatic ring are all carbon atoms. The carbon atoms are optionally substituted with preferred groups as described for aryl groups above.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazoyl, and the like, all optionally substituted.

The term "heteroatom-unsubstituted C$_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted C$_6$-C$_{10}$-aryl has 6 to 10 carbon atoms. Examples of heteroatom-unsubstituted aryl groups include phenyl, methylphenyl, (dimethyl)phenyl, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CH$_3$, naphthyl, quinolyl, indolyl, and the radical derived from biphenyl. The term "heteroatom-unsubstituted aryl" includes carbocyclic aryl groups, biaryl groups, and radicals derived from polycyclic fused hydrocarbons (PAHs).

The term "heteroatom-substituted C$_n$-aryl" refers to a radical, refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted C$_1$-C$_{10}$-heteroaryl has 1 to 10 carbon atoms. The term "heteroatom-substituted aryl" includes heteroaryl and heterocyclic aryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —C$_6$H$_4$F, —C$_6$H$_4$Cl, —C$_6$H$_4$Br, —C$_6$H$_4$OH, —C$_5$H$_4$OCH$_3$, —C$_6$H$_4$OCH$_2$CH$_3$, —C$_6$H$_4$OCOCH$_3$, —C$_6$H$_4$OC$_6$H$_5$, —C$_6$H$_4$NH$_2$, —C$_6$H$_4$NHCH$_3$, —C$_6$H$_4$NHCH$_2$CH$_3$, —C$_6$H$_4$CH$_2$Cl, —C$_6$H$_4$CH$_2$Br, —C$_6$H$_4$CH$_2$H$_4$NH$_2$, —C$_6$H$_4$CH$_2$OCOCH$_3$, —C$_6$H$_4$CH$_2$NH$_2$, —C$_6$H$_4$N(CH$_3$)$_2$, —C$_6$H$_4$CH$_2$CH$_2$Cl, —C$_6$H$_4$CH$_2$CH$_2$OH, —C$_6$H$_4$CH$_2$CH$_2$OCOCH$_3$, —C$_6$H$_4$CH$_2$CH$_2$NH$_2$, —C$_6$H$_4$CH$_2$CH=CH$_2$, —C$_6$H$_4$CF$_3$, —C$_6$H$_4$CN, —C$_6$H$_4$C—CSi(CH$_3$)$_3$, —C$_6$H$_4$COH, —C$_6$H$_4$COCH$_3$, —C$_6$H$_4$COCH$_2$CH$_3$, —C$_6$H$_4$COCH$_2$CF$_3$, —C₆H₄COC₆H₅, —C₆H₄CO₂H, —C₆H₄CO₂CH₃, —C₆H₄CONH₂, —C₆H₄CONHCH₃, —C₆H₄CON(CH₃)₂, furanyl, thienyl, pyridyl, pyrrolyl, pyrimidyl, pyrazinyl, and imidazoyl.

The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. An "aralkyl" includes an alkyl heteroatom-substituted with an aryl group. Examples of heteroatom-unsubstituted aralkyls include phenylmethyl (benzyl) and phenylethyl.

The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated in an aromatic ring structure, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —COCH₃, —COCH₂CH₃, —COCH₂CH₂CH₃, —COCH(CH₃)₂, —COCH(CH₂)₂, —COC₆H₅, —COC₆H₄CH₃, —COC₆H₄CH₂CH₃, —COC₆H₄CH₂CH₂CH₃, —COC₆H₄CH(CH₃)₂, —COC₆H₄CH(CH₂)₂, and —COC₆H₃(CH₃)₂, are examples of heteroatom-unsubstituted acyl groups.

The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —COCH₂CF₃, —CO₂H, —CO₂CH₃, —CO₂CH₂CH₃, —CO₂CH₂CH₂CH₃, —CO₂CH(CH₃)₂, —CO₂CH(CH₂)₂, —CONH₂, —CONHCH₃, —CONHCH₂CH₃, —CONHCH₂CH₂CH₃, —CONHCH(CH₃)₂, —CONHCH(CH₂)₂, —CON(CH₃)₂, —CON(CH₂CH₃)CH₃, —CON(CH₂CH₃)₂ and —CONHCH₂CF₃, are examples heteroatom-substituted acyl groups.

An "alkoxy" group refers to an "—O-alkyl" group, where "alkyl" is defined above.

An "aryl" group refers to an aromatic group which has at least one ring having a conjugated pi electron system, and includes carbocyclic aryl, heterocyclic aryl, and biaryl groups, all of which may be optionally substituted. Preferably, the aryl is a substituted or unsubstituted phenyl or pyridyl. Preferred aryl substituent(s) are halogen, trihalomethyl, hydroxyl, SH, OH, NO₂, amine, thioether, cyano, alkoxy, alkyl, and amino groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH₃, —OCH₂CH₃, —OCH₂CH₂CH₃, —OCH(CH₃)₂, and —OCH(CH₂)₂.

The term "heteroatom-substituted $C_n$-alkoxy" refers to a group, having the structure —OR, in which R is a heteroatom-substituted $C_n$-alkyl, as that term is defined above. For example, —OCH₂CF₃ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above.

The term "heteroatom-substituted $C_n$-alkenyloxy" refers to a group, having the structure —OR, in which R is a heteroatom-substituted $C_n$-alkenyl, as that term is defined above.

The term "heteroatom-unsubstituted $C_n$-alkynyloxy" refers to a group, having the structure —OR, in which R is a heteroatom-unsubstituted $C_n$-alkynyl, as that term is defined above.

The term "heteroatom-substituted $C_n$-alkynyloxy" refers to a group, having the structure —OR, in which R is a heteroatom-substituted $C_n$-alkynyl, as that term is defined above.

The term "heteroatom-unsubstituted $C_n$-aryloxy" refers to a group, having the structure —OAr, in which Ar is a heteroatom-unsubstituted $C_n$-aryl, as that term is defined above. An example of a heteroatom-unsubstituted aryloxy group is —OC₆H₅.

The term "heteroatom-substituted $C_n$-aryloxy" refers to a group, having the structure —OAr, in which Ar is a heteroatom-substituted $C_n$-aryl, as that term is defined above.

The term "heteroatom-unsubstituted $C_n$-aralkyloxy" refers to a group, having the structure —OAr, in which Ar is a heteroatom-unsubstituted $C_n$-aralkyl, as that term is defined above.

The term "heteroatom-substituted $C_n$-aralkyloxy" refers to a group, having the structure —OAr, in which Ar is a heteroatom-substituted $C_n$-aralkyl, as that term is defined above.

The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —OCOCH₃ is an example of a heteroatom-unsubstituted acyloxy group.

The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH₃, —NHCH₂CH₃, —NHCH₂CH₂CH₃, —NHCH(CH₃)₂, —NHCH(CH₂)₂, —NHCH₂CH₂CH₂CH₃, —NHCH(CH₃)

$CH_2CH_3$, —$NHCH_2CH(CH_3)_2$, —$NHC(CH_3)_3$, —$N(CH_3)_2$, —$N(CH_3)CH_2CH_3$, —$N(CH_2CH_3)_2$, N-pyrrolidinyl, and N-piperidinyl.

The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted $C_n$-alkenylamino groups also include dialkenylamino and alkyl(alkenyl)amino groups.

The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atom, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl(alkynyl)amino groups.

The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups.

The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups.

The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above. The term "heteroatom-substituted aralkylamino" includes the term "heteroaralkylamino."

The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The term amido includes N-alkyl-amido, N-aryl-amido, N-aralkyl-amido, acylamino, alkylcarbonylamino, arylcarbonylamino, and ureido groups. The group, —NHCOCH$_3$, is an example of a heteroatom-unsubstituted amido group.

The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

The term "heteroatom-unsubstituted $C_n$-sulfonamido" refers to a radical, having a single nitrogen atom as the point of attachment, further having a sulfonyl group attached via its sulfur atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term amido includes N-alkyl-sulfonamido, N-aryl-sulfonamido, N-aralkyl-sulfonamido, sulfonylamino, alkylsulfonamino, and arylsulfonamino groups. The group, —NHS(O)$_2$CH$_3$, is an example of a heteroatom-unsubstituted sulfonamido group.

The term "heteroatom-substituted $C_n$-sulfonamido" refers to a radical, having a single nitrogen atom as the point of attachment, further having a sulfonyl group attached via its sulfur atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the sulfur and oxygen atoms of the sulfonyl group, wherein each additional heteroatom is independently selected from the group consisting of N, O, F, Cl, Br, I, Si, P, and S. For example, a heteroatom-substituted $C_1$-$C_{10}$-sulfonamido has 1 to 10 carbon atoms. The group, —NHS(O)$_2$OCH$_3$, is an example of a heteroatom-substituted sulfonamido group.

The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group.

The term "heteroatom-substituted $C_n$-alkylthio" refers to a group, having the structure —SR, in which R is a heteroatom-substituted $C_n$-alkyl, as that term is defined above.

The term "heteroatom-unsubstituted $C_n$-alkenylthio" refers to a group, having the structure —SR, in which R is a heteroatom-unsubstituted $C_n$-alkenyl, as that term is defined above.

The term "heteroatom-substituted $C_n$-alkenylthio" refers to a group, having the structure —SR, in which R is a heteroatom-substituted $C_n$-alkenyl, as that term is defined above.

The term "heteroatom-unsubstituted $C_n$-alkynylthio" refers to a group, having the structure —SR, in which R is a heteroatom-unsubstituted $C_n$-alkynyl, as that term is defined above.

The term "heteroatom-substituted $C_n$-alkynylthio" refers to a group, having the structure —SR, in which R is a heteroatom-substituted $C_n$-alkynyl, as that term is defined above.

The term "heteroatom-unsubstituted $C_n$-arylthio" refers to a group, having the structure —SAr, in which Ar is a heteroatom-unsubstituted $C_n$-aryl, as that term is defined above. The group, —SC$_6$H$_5$, is an example of a heteroatom-unsubstituted arylthio group.

The term "heteroatom-substituted $C_n$-arylthio" refers to a group, having the structure —SAr, in which Ar is a heteroatom-substituted $C_n$-aryl, as that term is defined above.

The term "heteroatom-unsubstituted $C_n$-aralkylthio" refers to a group, having the structure —SAr, in which Ar is a heteroatom-unsubstituted $C_n$-aralkyl, as that term is defined above. The group, —SCH$_2$C$_6$H$_5$, is an example of a heteroatom-unsubstituted aralkyl group.

The term "heteroatom-substituted $C_n$-aralkylthio" refers to a group, having the structure —SAr, in which Ar is a heteroatom-substituted $C_n$-aralkyl, as that term is defined above.

The term "heteroatom-unsubstituted $C_n$-acylthio" refers to a group, having the structure —SAc, in which Ac is a heteroatom-unsubstituted $C_n$-acyl, as that term is defined above. The group, —SCOCH$_3$, is an example of a heteroatom-unsubstituted acylthio group.

The term "heteroatom-substituted $C_n$-acylthio" refers to a group, having the structure —SAc, in which Ac is a heteroatom-substituted $C_n$-acyl, as that term is defined above.

The term "heteroatom-unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted $C_1$-$C_{10}$-alkylsilyl has 1 to 10 carbon atoms. An alkylsilyl group includes dialkylamino groups. The groups, —Si(CH$_3$)$_3$ and —Si(CH$_3$)$_2$C(CH$_3$)$_3$, are examples of heteroatom-unsubstituted alkylsilyl groups.

The term "heteroatom-substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts are known to one of ordinary skill in the art.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use-A Handbook (2002), which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "$IC_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein the specification, "a" or "an" may mean one or more. As used herein in the claim(s), when used in conjunction with the word "comprising" or "having," the words "a" or "an" may mean one or more than one. As used herein "another" may mean at least a second or more.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-$\beta$, transforming growth factor-$\beta$; IFN-$\gamma$, interferon-$\gamma$; LPS, bacterial endotoxic lipopolysaccharide; TNF-$\alpha$, tumor necrosis factor-$\alpha$; IL-1$\beta$, interleukin-1$\beta$; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds provided herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds as described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug.

Furthermore, a wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

While it may be possible for the compounds of the subject invention to be administered as the raw chemical, it is also possible to present them as a pharmaceutical formulation. Accordingly, the subject invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Preferred unit dosage formulations are those containing an effective dose, as herein below recited, or an appropriate fraction thereof, of the active ingredient.

It should be understood that in addition to the ingredients particularly mentioned above, the formulations may include other agents conventional in the art having regard to the type of formulation in question, for example those suitable for oral administration may include flavoring agents.

The compounds provided herein can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In short, the compounds of the invention may be administered orally, topically, or by injection at a dose of from 0.1 to 500 mg/kg per day. Tablets or other forms of presentation provided in discrete units may conveniently contain an amount of compound of the invention which is effective at such dosage or as a multiple of the same, for instance, units containing 5 mg to 500 mg.

The amount of active ingredient that may be combined with the carrier materials to produce a single dosage form will vary depending upon the host treated and the particular mode of administration.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for cancer involving administration of one of the compounds described herein, increased therapeutic benefit may result by also providing the patient with another therapeutic agent for cancer. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound provided herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, methods for treating STAT3-mediated disorders or conditions (as well as STAT5-mediated disorders or conditions) in a human or animal subject in need of such treatment comprise administering to the subject an amount of a compound presented herein effective to reduce or prevent said disorder in the subject in combination with at least one additional agent for the treatment of said disorder that is known in the art. In a related aspect, therapeutic compositions comprise at least one these compounds in combination with one or more additional agents for the treatment of STAT3- and STAT5-mediated disorders.

The compounds described herein may be useful for the treatment of a wide variety of disorders or conditions where inhibition or modulation of the STAT3 pathway is needed. The compounds decrease and can therapeutically treat proliferative disease conditions. Uses for these compounds include the compounds as agents to: decrease STAT3 activity; STAT3 phosphorylation; and the expression of proteins controlled by transcriptional activation by activated STAT3. Along these lines, the compounds can be specifically used as agents to decrease VEGF, MMP9, MMP2, survivin, c-Myc, MMP-1, MEK-5, c-FOS,1 COX-2, Bcl-x1, MMP-10, HSP-27 and Jmjd1a.

Disorders or conditions that can be prevented or treated by compounds and methods described herein include the prevention or treatment of cancer, such as cutaneous T-cell leukemia, head and neck tumors, pancreatic cancer, bladder cancer, high grade gliomas, brain metastasis, melanoma, skin cancer, lung cancer, breast cancer, prostate cancer, colon cancer, leukemia, myelodysplastic syndrome (a pre-leukemia condition), and multiple myeloma. In general, metastasis of any cancer can be prevented or treated with the compounds and methods described herein. The compounds can also be used to prevent or treat proliferative angiogenic conditions including telangectasia, venous angiomas, hemangioblastoma.

These compounds and methods can also be used to prevent or treat proliferative diseases or disorders of the skin, including topical dermatitis, psoriasis, and rosacea.

Furthermore, the compounds and methods that are described herein can be used to prevent or treat Central Nervous System ("CNS") diseases and conditions such as CNS inflammatory and conditions, e.g., multiple sclerosis and progressive multifocal leukoencephalopathy.

Moreover, the compounds and methods that are described herein can be used to prevent or treat inflammatory diseases and conditions, such as osteoarthritis, Rheumatoid arthritis, Crohn's disease, ulcerative colitis, and auto-immune diseases such as lupus and mixed auto-immune disease.

Diseases and conditions such as telangectasia, venous angiomas, hemangioblastoma, and polycythemia vera may also be advantageously prevented or treated with the compounds and methods described herein.

These compounds and methods can affect stem cell survival and differentiation by maintaining stem cell sternness, e.g., preventing the differentiation of stem cells.

The compounds taught herein may also be used for the augmentation of immune response, particularly where the augmentation of the immune response leads to the expression of costimulatory molecules on the peripheral macrophages and tumor-infiltrating microglia. These compounds are also useful when the immune response leads to proliferation of effector T cells and/or up-regulation of several key intracellular signaling molecules that critically regulate T-cell and monocyte activation. The compounds are useful when the immune responses leads to up-regulation of several key intracellular signaling molecules that critically regulate T-cell and monocyte activation, particularly phosphorylation of Syk (Tyr(352)) in monocytes and ZAP-70 (Tyr (319)) in T cells.

Table 1 as found immediately below describes certain of the diseases and conditions that may be treated using the compounds described herein:

TABLE 1

Activation of STATs in Human Cancers

| Tumor Type | Activated STAT |
| --- | --- |
| Blood Tumors | |
| Multiple myeloma | STAT1, STAT3 |
| Leukaemias: | |
| HTLV-1-dependent | STAT3, STAT5 |
| Erythroleukaemia | STAT1, STAT5 |
| Acute myelogenous leukaemia (AML) | STAT1, STAT3, STAT5 |
| Chronic myelogenous leukaemia (CML) | STAT5 |
| Large granular lymphocyte leukaemia (LGL) | STAT3 |
| Lymphomas: | |
| EBV-related/Burkitt's | STAT3 |
| Mycosis fungoides | STAT3 |
| Cutaneous T-cell lymphoma | STAT3 |
| Non-Hodgkins lymphoma (NHL) | STAT3 |
| Anaplastic large-cell lymphoma (ALCL) | STAT3 |
| Solid Tumors | |
| Breast Cancer | STAT1, STAT3, STAT5 |
| Head and neck cancer | STAT1, STAT3, STAT5 |
| Melanoma | STAT3 |
| Ovarian cancer | STAT3 |
| Lung cancer | STAT3 |
| Pancreatic cancer | STAT3 |
| Prostate cancer | STAT3 |
| Glioma | STAT3, STAT5 |

Based on references cited in REFS 12, 17, EBV, Epstein-Barr virus; HTLV-1, human T-lymphotrophic virus-1.

The STAT ("signal transducer and activator of transcription") protein family includes transcription factors which are specifically activated to regulate gene transcription when cells encounter cytokines and growth factors. In mammals, there are seven known members of the STAT family of proteins: STAT1, STAT2, STAT3, STAT4, STAT5a, STAT5b, and STATE. Yu, H., Jove, R., *The STATS of Cancer—New Molecular Targets Come of Age*, Nature Reviews, 4:97-105 (2004). These seven proteins range in size from 750 and 850 amino acids. The STAT5a and STAT5b proteins, collectively referred to herein as "STAT5," are closely related but encoded by different genes. Yu, H., Jove, R., *The STAT5 of Cancer—New Molecular Targets Come of Age*, Nature Reviews, 4:97-105 (2004).

STAT proteins act as signal transducers in the cytoplasm and transcription activators in the nucleus. Kisseleva T., Bhattacharya S., Braunstein J., Schindler C. W., *Signaling Through the JAK/STAT Pathway, Recent Advances and Future Challenges*, Gene 285: 1-24 (2002). For example, STAT proteins transduce signals from cytokine receptors, growth factor receptors, and non-receptor, cytoplasmic tyrosine kinases such as Src and Abl to the nucleus of a cell, where they bind DNA and regulate transcription of an assoiment of genes. Id. As a result, STAT proteins regulate physiological functions such as immune response, inflammation, proliferation, differentiation, survival, metastasis, apoptosis, and immuno tolerance (e.g. tumor immune evasion). Xie, T. et al., *Stat3 Activation Regulates the Expression of Matrix Metalloproteinase-2 and Tumor Invasion and Metastasis*, Oncogene 23: 3550-3560 (2004); Levy, D. E., Inghirami, G., *STAT3: A Multifaceted Oncogene*, PNAS 103: 10151-52 (2006).

STATs share structurally and functionally conserved domains including: an N-terminal domain that strengthens interactions between STAT dimers on adjacent DNA-binding sites; a coiled-coil STAT domain that is implicated in protein-protein interactions; a DNA-binding domain with an immunoglobulin-like fold similar to p53 tumor suppressor protein; an EF-hand-like linker domain connecting the DNA-binding and SH2 domains; an SH2 domain that acts as a phosphorylation-dependent switch to control receptor recognition and DNA-binding; and a C-terminal transactivation domain. Chen X., Vinkemeier U., Zhao Y., Jeruzalmi D., Darnell J. E., Kuriyan J., *Crystal Structure of a Tyrosine Phosphorylated STAT-1 Dimer Bound to DNA*, Cell 93: 827-839 (1998). In order to bind DNA, STAT proteins must dimerize. Yu, H., Jove, R., *The STAT5 of Cancer—New Molecular Targets Come of Age*, Nature Reviews, 4:97-105 (2004), Darnell, J. Jr., *Validating Stat3 in Cancer Therapy*, Nature Medicine, 11:595-96 (2005). Dimer formation involves reciprocal interaction between a SRC-homology 2 (SH2) domain of one STAT molecule with a phosphotyrosine residue of a second STAT molecule.

STAT proteins have been found to be overactive and/or persistently activate in cancer cells, including solid tumors and blood malignancies, proliferative diseases of the skin, and inflammatory diseases. Yu, H., Jove, R., *The STAT5 of Cancer—New Molecular Targets Come of Age*, Nature Reviews, 4:97-105 (2004). For example, STAT signaling has been implicated in various cancers. Song, J. I. and Grandis, J. R., *STAT Signaling in Head and Neck Cancer*, Oncogene, 19: 2489-2495, 2000; Nikitakis, N. G. et al., *Targeting the STAT Pathway in Head and Neck Cancer: Recent Advances and Future Prospects*, Current Cancer Drug Targets, 4:639-651. An increased presence of activated STAT3 and/or STAT5 in the nucleus is associated with dysregulation of gene transcription. Yu, H., Jove, R., *The STAT5 of Cancer—New Molecular Targets Come of Age*, Nature Reviews, 4:97-105. Further, an increased presence of STAT3 and/or STAT5 is associated with increased transcription of genes which contribute to a cell proliferation, survival, angiogenesis, and tumor-induced immunotolerance. Yu, H., Jove, R., *The STAT5 of Cancer—New Molecular Targets Come of Age*, Nature Reviews, 4:97-105. For example, STAT5 is activated in certain leukemias, breast cancer, and head and neck cancer. Yu, H., Jove, R., *The STAT5 of Cancer—New Molecular Targets Come of Age*, Nature Reviews, 4:97-105. Similarly, STAT3 activation is known to abrogate growth factor dependence which contributes to certain carcinoma tumor growth. Kijima, T., Niwa, H., Steinman, R. A., Drenning, S. D., Gooding, W. E., Wentzel, A. L., Xi, S., and Grandis, J. R., *STAT3 Activation Abrogates Growth Factor Dependence And Contributes To Head And Neck Squamous Cell Carcinoma Tumor Growth In Vivo*, Cell Growth Differ, 13: 355-362, 2002. Activation of STAT3 is also reported to regulate survival in human non-small cell carcinoma cells. Song, L., Turkson, J., Karras, J. G., Jove, R., and Haura, E. B., *Activation Of Stat3 By Receptor Tyrosine Kinases And Cytokines Regulates Survival In Human Non-Small Cell Carcinoma Cells*, Oncogene, 22: 4150-4165, 2003. Accordingly, STAT3 and STAT5 are useful targets in treating STAT3- and STAT5-mediated disease.

Both STAT3- and STAT5-signaling pathways involve binding of cytokines or growth factors to cell-surface receptors, which leads to activation of cytoplasmic tyrosine kinases, such as the JAK family, which subsequently leads to phosphorylation of STAT monomers. Gadina, M., Hilton, D., Johnston, J. A., Morinobu, A., Lighvani, A., Zhou, Y. J., Visconti, R., O'Shea, J. J. *Signaling by Type I and Type II Cytokine Receptors: Ten Years After*, Curr. Opin. Immunol. 2001, 13: 363. STAT proteins are activated by phosphorylation causing them to dimerize and translocate to the nucleus, where they bind to specific promoter sequences in target genes. Horvath, C. M., *The Jak-STAT Pathway Stimulated by Interferon Gamma*, Science, STKE, 2004, 260: tr8.

Figure 5:
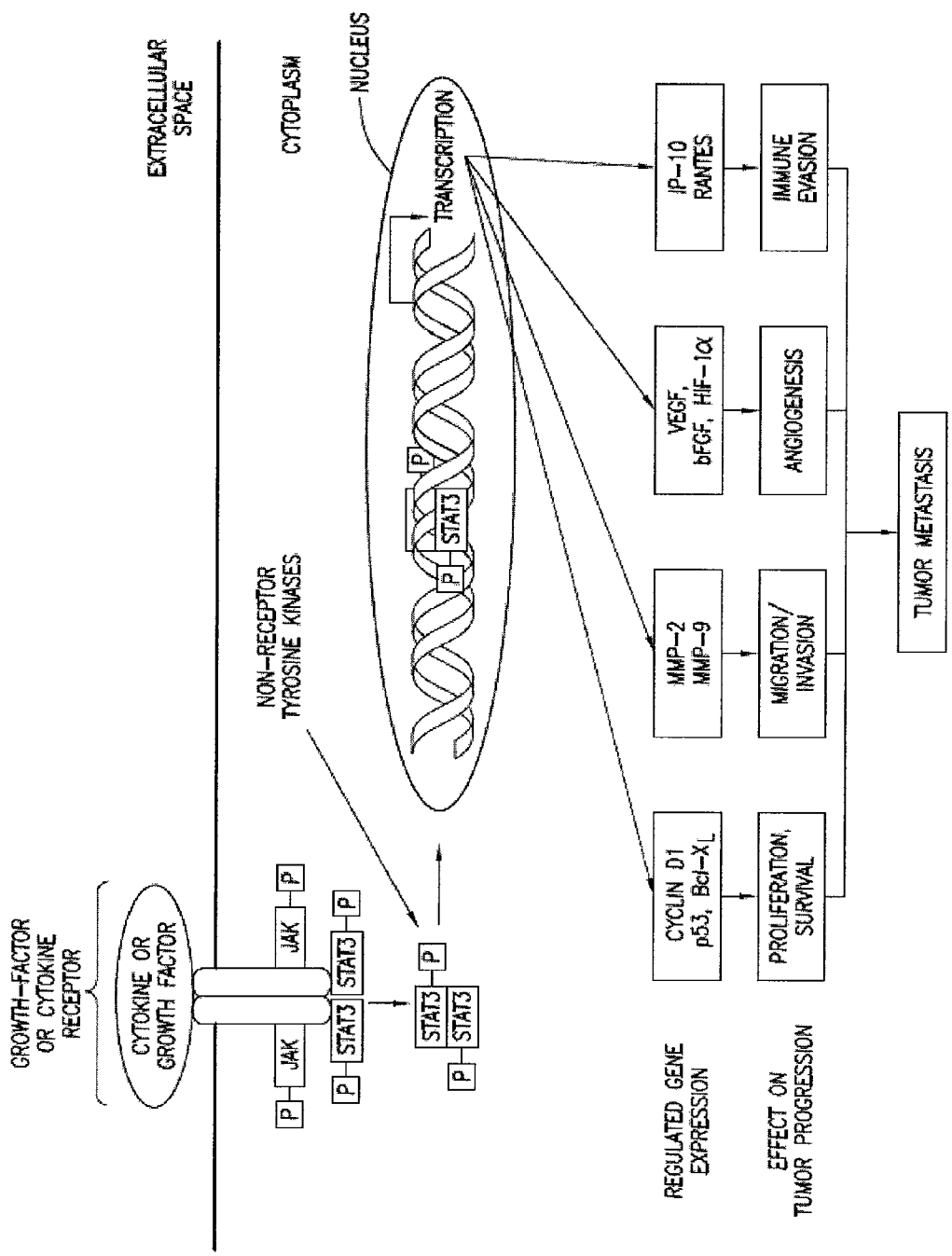
FIG. 5 is a schematic representation of signaling pathways which lead to STAT activation and STAT-mediated gene expression.

As shown schematically in FIG. 5, growth factor receptors, cytokine receptors and non-receptor tyrosine kinases have signaling pathways that converge on STAT3 and STAT5. For STAT3, these receptors and kinases include IL-2, IL-6, IL-7, IL-9, IL-10, IL-11, IL-15, IL-21, EGF, OSM, G-CSF, TPO, LIF and GH. For STAT5, the receptors and kinases include IL-2, IL-3, IL-5, IL-7, IL-9, IL-15, G-CSF, GM-CSF, EPO, TPO, GH, and PRL.

More specifically, STAT3 activation is known to be mediated by EGFR, EPO-R, and IL-6 R via c-Src or JAK2. See e.g., Lai, S. Y., Childs, E. E., Xi, S., Coppelli, F. M., Gooding, W. E., Wells, A., Ferris, R. L., and Grandis, J. R., *Erythropoietin-Mediated Activation of JAK-STAT Signaling Contributes to Cellular Invasion in Head and Neck Squamous Cell Carcinoma*, Oncogene, 24: 4442-4449, 2005; Siavash, H., Nikitakis, N. G., and Sauk, J. J., *Abrogation of IL-6-Mediated JAK Signalling by the Cyclopentenone Prostaglandin 15d-PGJ(2) in Oral Squamous Carcinoma Cells*, Br J Cancer, 91: 1074-1080, 2004; & Quadros, M. R., Peruzzi, F., Kari, C., and Rodeck, U., *Complex Regulation of Signal Transducers and Activators of Transcription 3 Activation in Normal and Malignant Keratinocytes*, Cancer Res, 64: 3934-3939, 2004. MAPK activation can lead to decreased STAT3 phosphorylation. In solid tumors, PDGFR and c-Met can also activate STAT3 via c-Src. IGFR1 and EGFR can activate STAT3 in a JAK-independent manner. STAT3 activation can lead to activation of several downstream target genes including Bcl-XL, cyclin D1 and VEGF.

Ligand binding to a cell-surface cytokine receptor triggers activation of JAKs. With increased kinase activity, JAK phosphorylates tyrosine residues on the receptor and creates sites for interaction with proteins that contain phosphotyrosine-binding SH2 domain. STATs possessing SH2 domains capable of binding these phosphotyrosine residues are recruited to the receptors and are tyrosine-phosphorylated by JAKs. The phosphotyrosine then acts as a docking site for SH2 domains of other STATs, mediating their dimerization. Different STATs form hetero- as well as homodimers. Activated STAT dimers accumulate in the cell nucleus and activate transcription of their target genes. Hebenstreit D. et al. (2005) Drug News Perspect. Vol. 18 (4), pages 243-249. STATs can be tyrosine-phosphorylated by other non-receptor tyrosine kinases, such as c-src, as well as receptor tyrosine kinases, such as the epidermal growth factor receptor.

Likewise, the binding of IL-6 family cytokines (including IL-6, oncostatin M and leukemia inhibitory factor) to the gp130 receptor triggers STAT3 phosphorylation by JAK2. Boulton, T G, Zhong, Z, Wen, Z, Darnell, Jr, J E, Stahl, N, and Yancopoulos, G D, *STAT3 Activation by Cytokines Utilizing gp130 and Related Transducers Involves a Secondary Modification Requiring an H7-Sensitive Kinase* Proc Natl Acad Sci USA. 92(15): 6915-6919. EGF-R and certain other receptor tyrosine kinases, such as c-MET phosphorylate STAT3 in response to their ligands. Yuan Z L et al., (2004) Mol. Cell Biol. Vol. 24 (21), pages 9390-9400. STAT3 is also a target of the c-src non-receptor tyrosine kinase. Silva C. M. (2004) Oncogene Vol. 23 (48), pages 8017-8023. In addition to STAT3 activation through IL-6 binding, STAT3 is further activated by binding of IL-2, IL-7, IL-9, IL-10, IL-11, IL-15, IL-21, EGF, OSM, G-CSF, TPO, LIF, or GH to an appropriate receptor. Similarly, STAT5 is activated by binding of IL-2, IL-3, IL-5, IL-7, IL-9, IL-15, G-CSF, GM-CSF, EPO, TPO, GH, or PRL to an appropriate receptor.

Indeed, Janus kinases ("JAK") play an important role in the initial steps of cytokine receptor signaling. While the specificity of the four members of the JAK family (Jak1, Jak2, Jak3, and Tyk2) for different cytokine receptors is not fully understood, studies report that certain specific cytokine receptors can activate one or more Jak. O'shea, J. J., Pesu, M., Borie, D. C., Changelian, P. S., *A New Modality for Immunosuppression: Targeting the JAK/STAT Pathway*, Nature Rev. Drug Disc. 2004 (3): 555-564. For example, the growth hormone receptor (GHR) may interact predominantly with Jak2, and has been shown that to induce phosphorylation of Jak1 and Jak3. Hellgren, G., Jansson, J. O., Carlsson, L. M., Carlsson, B., *The Growth Hormone Receptor Associates with Jak1, Jak2 and Tyk2 in Human Liver*, Growth Horm. IGF Res. 1999 9(3):212-8.

The JAK-STAT pathway can be negatively regulated on multiple levels. Protein tyrosine phosphatases remove phosphates from cytokine receptors as well as activated STATs Hebenstreit D. et al. (2005) Drug News Perspect. Vol. 18 (4), pages 243-249. More recently, identified Suppressors of Cytokine Signaling (SOCS) inhibit STAT phosphorylation by binding and inhibiting JAKs or competing with STATs for phosphotyrosine binding sites on cytokine receptors. Krebs, L. et al. (2001) Stem Cells Vol. 19, pages 378-387. STATs are also negatively regulated by Protein Inhibitors of Activated STATs (PIAS), which act in the nucleus through several mechanisms. Shuai, K. (2006) Vol. 16 (2), pages 196-202. For example, PIAS 1 and PIAS3 inhibit transcriptional activation by STAT1 and STAT3 respectively by binding and blocking access to the DNA sequences they recognize.

The JAK-STAT signaling pathway takes part in the regulation of cellular responses to cytokines and growth factors. Employing Janus kinases (JAKs) and Signal Transducers and Activators of Transcription (STATs), the pathway transduces the signal carried by these extracellular polypeptides to the cell nucleus, where activated STAT proteins modify gene expression. Although STATs were originally discovered as targets of Janus kinases, certain stimuli can activate them independent of JAKs. D W Leaman, S Pisharody, T W Flickinger, M A Commane, J Schlessinger, I M Kerr, D E Levy, and G R Stark *Roles of JAKs in Activation of STATs and Stimulation of c-fos Gene Expression by Epidermal Growth Factor*, Mol Cell Biol. 1996 16(1): 369-375. This pathway plays a central role in principal cell fate decisions, regulating the processes of cell proliferation, differentiation and apoptosis. STAT activator phosphorylation requires phosphorylation of JAK to phosphorylate. In other words, JAK must first phosphorylate and bind to STAT. STAT is then able to phosphorylate and dimerize with another STAT.

The compounds described herein can control cell growth and survival via STAT modulation. Cell activity is regulated by "signals." Signals enter cell walls through receptors, Signals are transduced by STATs. STATs complete a pathway to DNA. Signals activate DNA transcription (otherwise referred to as gene activation). BCL-X1, MCL1, Surivin and p53 are involved in cell survival. MYC, Cyclin D1/D2 and p53 are involved in cell proliferation. Downstream of the phosphorylation of STAT3, signaling pathways cause angiogensis as a result of regulation of VEGF, H1F1 and p53, and immune evasion as regulated by immune-suppressing factors, pro-inflammatory cytokines and pro-inflammatory chemokines.

The compounds and methods described herein can directly or indirectly modulate STAT3 and/or STAT5 activation. For example, the compounds and methods can inhibit STAT3 activation by: (1) affecting signaling pathways which lead to STAT3 or STAT5 activation, such that the downstream activation of STAT3 or STAT5 is prevented or reduced; (2) directly preventing or reducing STAT3 or STAT5 activation, e.g., by preventing phosphorylation of STAT3 or STAT5; and (3) disrupting complexation of STAT3 or STAT5 with any number of cofactors and/or macromolecules, where the complexes are responsible for regulation of STAT3 or STAT5 signaling, and likewise STAT5 activation.

Inhibition of STAT3 and/or STAT5 activation can be accomplished, directly or indirectly, through any of the STAT targeting strategies currently known in the art. By way of example only, STAT3 activity might be decreased by: (1) reducing the availability of STAT3 or STAT5 molecules for recruitment; (2) blocking STAT3 or STAT5 recruitment to receptors, (3) blocking phosphorylation of STAT3 or STAT5 molecules; (4) interfering with the formation of STAT3 or STAT5 dimers; (5) interference with translocation of STAT3 or STAT5 dimers into the nucleus; (6) interference of STAT3 or STAT5 binding to DNA; (7) interference of STAT3 or STAT5 interaction with transcriptional activators; and/or (8) other methods of preventing STAT-mediated transcriptional activation. See e.g., N. G. Nikitakis, et al., *Targeting the STAT Pathway in Head and Neck Caner: Recent Advances and Future Prospects*, Current Cancer Drug Targets, 4: 637-651 (2004).

Direct or indirect modulation of STAT3 or STAT5 activity by the compounds presented herein can prevent, reduce, or eliminate STAT3- and/or STAT5-dependent activation of genes responsible for proliferation, survival, metastasis, angiogenesis, immune response, and tumor immune evasion. As shown schematically, in FIGS. 5 and 6, STAT3 and/or STAT5 activation have an effect on the transcription of many genes including, but not limited to, VEGF, MMP9, MMP2, survivin, c-Myc, MMP-1, MEK-5, c-FOS, COX-2, Bcl-xL, MMP-10, HSP27, Jmjd1a, PGE-2.

These activated STAT effects on the transcription of certain genes are likewise associated with physiological effects. For example, as reported by Yu and Jove at pages 99-101, which are incorporated by reference herein, activated STATs promote cell survival by up-regulating Bcl-xL, MCL1, and surviving, and down-regulating p53. Yu, H., et al., *The STATS of Cancer—New Molecular Targets Come of Age*, Nature Reviews, 4:97-105 (2004). Activated STATs also support proliferation by up-regulating MYC and cyclin D1/D2 and down-regulating p53. Additionally, activated STATs support angiogenesis through up-regulation of VEGF and HIF1, and down regulation of p53. Furthermore, activated STATs also aid tumor immune evasion by up-regulating immune-suppressing factors and down-regulating pro-inflammatory cytokines and chemokines.

Besides being useful for human treatment, the compounds and formulations of the present invention are also useful for veterinary treatment of companion animals, exotic animals and farm animals, including mammals, rodents, and the like. More preferred animals include horses, dogs, and cats.

General Synthetic Methods for Preparing Compounds

The following schemes can be used to practice the present invention.

Synthesis and Characterization

Synthesis of (E)-3-(6-bromopyridin-2-yl)acrylaldehyde

Solution of 6-bromo-2-carboxypyridine (3 g, 16.1 mmol) was dissolved in dichloromethane (100 mL). (Triphenylphosphoranylidene) acetaldehyde (4.9 g, 16.1 mmol) was added and obtained mixture was stirred at room temperature for 5 hrs. Dichloromethane was partially evaporated (to the volume about 50 mL) and reaction mixture was applied on chromatography column (SilicaGel 60) Products were eluted with dichloromethane. Fractions containing product were combined and evaporated to give 2.3 g of white powder (Yield 67%).

¹HNMR (CDCl3, δ) ppm: 9.81 (d, 1H, J=7.6 Hz, CHO), 7.63 (dd, 1H, J=J=7.7 Hz, H4), 7.51 (dd, 2H, J=J=7.7 Hz, H-3,5), 7.45 (d, 1H, J=15,8 Hz, Ar—CH═CH—CHO), 7.12 (dd, 1H, 1H, J=15.8 Hz, J=7.6 Hz, Ar—CH═CH—CHO)

General procedure: Synthesis of (2E,4E)-5-(6-bromopyridin-2-yl)-2-cyano-N-substituted-2,4-dienamides Solution of (1) (2.1 g, 9.9 mmol) and piperidine (0.2 mL) in anhydrous ethanol was prepared. Aldehyde (10.6 mmol) was added and reaction mixture was stirred at room temperature. After 3 hrs obtained solid was filtered, washed with ethanol and dried. The compounds as illustrated in the following examples were made.

EXAMPLE 1

(2E,4E)-5-(6-bromopyridin-2-yl)-2-cyano-N-[(1S)-1-phenylethyl]penta-2,4-dienamide

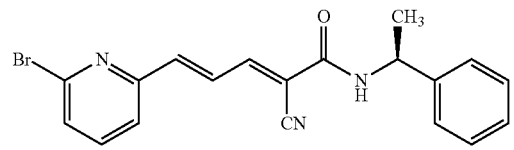

Yield 67% (2E,4E)-5-(6-bromopyridin-2-yl)-2-cyano-N-((S)-1-phenylethyl)penta-2,4-dienamide ¹HNMR (CDCl3, δ) ppm: 8.07 (d, 1H, J=12.1 Hz, H-3), 7.71 (dd, 1H, J=12.1 Hz, J=15.0 Hz, H-4), 7.59 (dd, 1H, J=J=7.7 Hz, H-4'), 7.47 (d, 1H, J=7.5 Hz, H-3'), 7.41 (d, 1H, J=7.63 Hz, H-5'), 7.39-7.29 (m, 5H, H aromat), 7.15 (d, 1H, J=15.0 Hz, H-5), 6.45 (d, 1 H, J=7.5 Hz, NH), 5.23 (dt, 1 H, J=7.0 Hz, J=7.5 Hz, H-1"), 1.61 9d, 1 H, J=7.0 Hz, Me).

EXAMPLE 2

(2E,4E)-5-(6-chloropyridin-2-yl)-2-cyano-N-[(1S)-1-phenylethyl]penta-2,4-dienamide

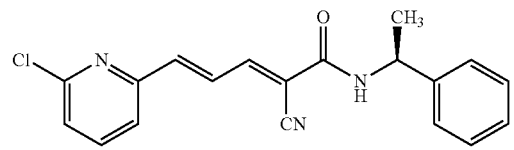

¹HNMR (CDCl3, δ) ppm: 8.07 (d, 1H, J=12.1 Hz, H-3), 7.73 (dd, 1H, J=12.0 Hz, J=15.0 Hz, H-4), 7.70 (dd, 1H, J=J=7.81 Hz, H-4'), 7.43-7.29(m, 7H, H-3', H-5', H aromat), 7.18 (d, 1H, J=15.0 Hz, H-5), 6.45 (d, 1H, J=7.3 Hz, NH), 5.25 (dt, 1H, J=7.0 Hz, J=7.5 Hz, H-1''), 1.61 (d, 1 H, J=7.0 Hz, Me).

EXAMPLE 3

(2E,4E)-5-(6-chloropyridin-2-yl)-2-cyano-N-[(1R)-1-phenylethyl]penta-2,4-dienamide

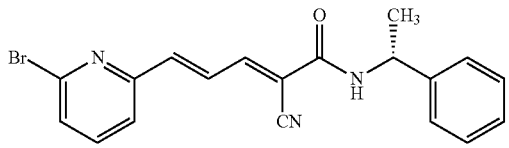

$^1$HNMR (CDCl3, δ) ppm: 8.07 (d, 1H, J=12.1 Hz, H-3), 7.71 (dd, 1H, J=12.1 Hz, J=15.0 Hz, H-4), 7.59 (dd, 1H, J=J=7.7 Hz, H-4'), 7.47 (d, 1H, J=7.5 Hz, H-3'), 7.41 (d, 1H, J=7.63 Hz, H-5'), 7.39-7.29(m, 5H, H aromat), 7.15 (d, 1H, J=15.0 Hz, H-5), 6.45 (d, 1 H, J=7.5 Hz, NH), 5.23 (dt, 1 H, J=7.0 Hz, J=7.5 Hz, H-1''), 1.61 (d, 1 H, J=7.0 Hz, Me).

EXAMPLE 4

(2E,4E)-N-benzyl-5-(6-bromopyridin-2-yl)-2-cyano-penta-2,4-dienamide

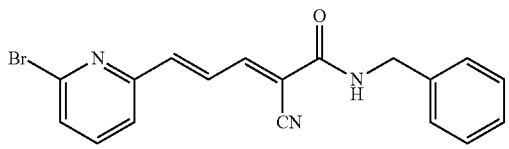

$^1$HNMR (CDCl3, δ) ppm: 8.10 (d, 1H, J=12.1 Hz, H-3), 7.70 (dd, 1H, J=12.1 Hz, J=15.0 Hz, H-4), 7.57 (d, 1H, J=7.7 Hz, H-4'), 7.46-7.29 (m, 7H, H-3', H-5', H aromat), 7.16 (d, 1H, J=15.0 Hz, H-5), 6.52 (bs, 1H, NH), 4.58 (d, 1H, J=5.8 Hz, 1'').

EXAMPLE 5

(2E,4E)-5-(6-chloropyridin-2-yl)-2-cyano-N-[(1R)-1-phenylethyl]penta-2,4-dienamide

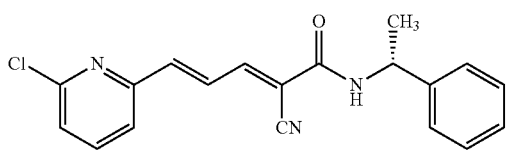

$^1$HNMR (CDCl3, δ) ppm: 8.07 (d, 1H, J=12.1 Hz, H-3), 7.73 (dd, 1H, J=12.0 Hz, J=15.0 Hz, H-4), 7.70 (dd, 1H, J=J=7.81 Hz, H-4'), 7.43-7.29(m, 7H, H-3', H-5', H aromat), 7.18 (d, 1H, J=15.0 Hz, H-5), 6.45 (d, 1H, J=7.3 Hz, NH), 5.25 (dt, 1H, J=7.0 Hz, J=7.5 Hz, H-1''), 1.61 (d, 1 H, J=7.0 Hz, Me).

EXAMPLE 6

(2E,4E)-N-benzyl-5-(6-chloropyridin-2-yl)-2-cyano-penta-2,4-dienamide

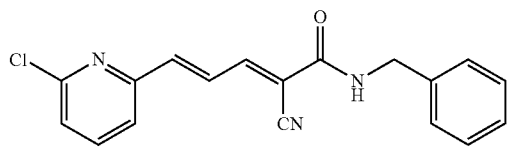

$^1$HNMR (CDCl3, δ) ppm: 8.09 (d, 1H, J=12.1 Hz, H-3), 7.72 (dd, 1H, J=12.1 Hz, J=15.0 Hz, H-4), 7.68 (dd, 1H, J=J=7.8 Hz, H-4'), 7.40-7.28 (m, 7H, H-3', H-5', H aromat), 7.17 (d, 1H, J=15.0 Hz, H-5), 6.45 (bs, 1H, NH), 4.58 (d, 1H, J=5.75 Hz, H-1'').

EXAMPLE 7

(2E,4E)-5-(6-bromopyridin-2-yl)-2-cyano-N—[(S)-cyclopropyl(phenyl)methyl]penta-2,4-dienamide

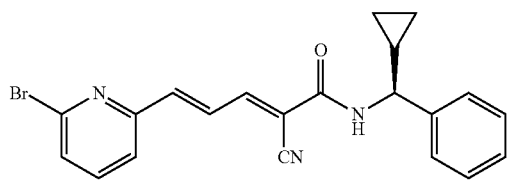

$^1$HNMR (CDCl3, δ) ppm: 8.06 (d, 1H, J=12.1 Hz, H-3), 7.72 (dd, 1H, J=12.1 Hz, J=15.0 Hz, H-4), 7.59 (dd, 1H, J=J=7.9 Hz, H-4'), 7.47-7.29 (m, 7H, H-3', H-5', H aromat), 7.15 (d, 1H, J=15.0 Hz, H-5), 6.68 (d, 1H, J=7.8 Hz, NH), 4.49 (dd, 1H, J=8.0 Hz, J=8.8 Hz, H-1''), 1.33-1.24 (m, 1 H, H-2''), 0.69-0.41 (m, 4H, 3''-CH$_2$, 4''-CH$_2$).

EXAMPLE 8

(2E,4E)-5-(6-bromopyridin-2-yl)-2-cyano-N-[(1S)-1-phenylpropyl]penta-2,4-dienamide

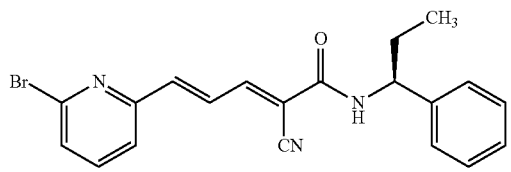

$^1$HNMR (CDCl3, δ) ppm: 8.03 (dd, 1H, J=12.1 Hz, J=0.7 Hz, H-3'), 7.69 (dd, 1H, J=12.1 Hz, J=15.0 Hz, H-4), 7.57 (dd, 1H, J=7.5 Hz, J=7.9 Hz, H-4'), 7.45 (dd, 1H, J=7.9 Hz, J=0.8 Hz, H-3), 7.39 (dd, 1H, J=7.5 Hz, J=0.8 Hz, H-5), 7.39-7.27 (m, 5H, H aromat), 7.1 (d, 1H, J=15.0 Hz, H-5), 6.43 (d, 1H, J=7.8 Hz, NH), 4.96 (dd, 1H, J=15.2 Hz, J=7.5 Hz, H-1"), 1.99-1.85 (m, 2H, H-2"), 0.93 (t, 3H, J=7.4 Hz, H-3").

EXAMPLE 9

(2E,4E)-5-(6-bromopyridin-2-yl)-2-cyano-N-[(1S)-1-phenylbutyl]penta-2,4-dienamide

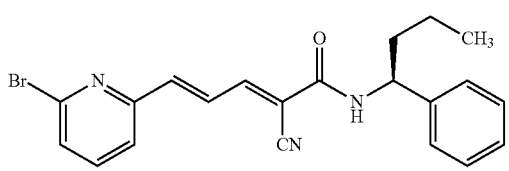

$^1$HNMR (CDCl3, δ) ppm: 8.03 (dd, 1H, J=12.1 Hz, J=0.7 Hz, H-3), 7.68 (dd, 1H, J=15.0 Hz, J=12.1 Hz, H-4), 7.55 (dd, 1H, J=J=7.7 Hz, H-4'), 7.45 (dd, 1H, J=7.9 Hz, J=0.8 Hz, H-3'), 7.39 (dd, 1H, J=7.5 Hz, J=0.8 Hz, H-5'), 6.66-7.28 (m, 6H, H-4, H-arom), 7.13 (d, 1H, J=14.9 Hz, H-5), 6.42 (d, 1H, J=8.0 Hz, NH), 5.05 (dd, 1H, J=15.3, J=7.6 Hz, H-1"), 1.91-1.82 (m, 2H, H-2"), 1.41-1.24 (m, 2H, H-3"), 0.95 (t, 3H, J=7.3 Hz, H-4").

The antiproliferative activity of the Compound of Example 1 and Example 7 have been shown in a Colo357FG pancreatic cancer cell line as follows:

| Compound | Colo357FG IC50 μM |
| --- | --- |
| Example 1 | 3.2 |
| Example 7 | 5.4 |

The activity of the compounds as STAT inhibitors in Examples 1, 2, 4, and 9 has been shown by at least one of the following assays. The associated activity data obtained is provided in FIGS. 1 through 4. The other compounds described above, which have not yet been made, are predicted to have activity in these assays as well.

Biological Activity Assay

MTT Method for Determining Cell Viability and Drug Dose-Response

A variety of cell types were seeded at a density of 50,000 cells/100 μl per well onto 96-well plates and cultured for 24-48 h in DMEM medium until they reached confluency. At confluency, 25 μl of fresh media containing WP1220 at various concentrations (0 to 100 μM) was added to the wells and incubated for 72 h at 37° C. The complex was removed, 100 μl of fresh medium was added and the cells were incubated overnight. Medium was removed and fresh medium (100 μl) was added to each well along with (20 μl) MTT solution (5 mg/ml in PBS) before incubating the cells for a further 4 h at 37° C. The reaction product was solubilised with sodium dodecyl sulfate (100 μl, 10%, w/v) in 0.01 N HCl overnight before quantifying the product using a microplate reader at 590 nm and comparing with control cells. The experiment was carried out in triplicate (n=3).

Biological Activity Assay

Western Blot Methods for Determining Protein and Phosphoprotein Content

Using phospho-tyrosine STAT3 (Y705), phospho-tyrosine Jak2 (Y1007/1008), total STAT3, total Jak2, Bcl-xL, actin (Cell Signaling Technology, Danvers, Mass.), and survivin (R&D Systems, Minneapolis, Minn.) antibodies, western blots were performed using the following methods. Briefly, (1) Samples were prepared from cells that were homogenized in a buffer protecting the protein of interest from degradation; (2) The sample was then separated using SDS-PAGE (10-15 μg protein/well) and then transferred to a membrane for detection; and (3) The membrane was incubated with a generic protein (milk proteins) to bind to any remaining sites on the membrane. A primary antibody was then added to the solution which is able to bind to its specific protein; (4) A secondary antibody-enzyme conjugate, which recognizes the primary antibody was then added to find locations where the primary antibody has bound.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound selected from the group consisting of:

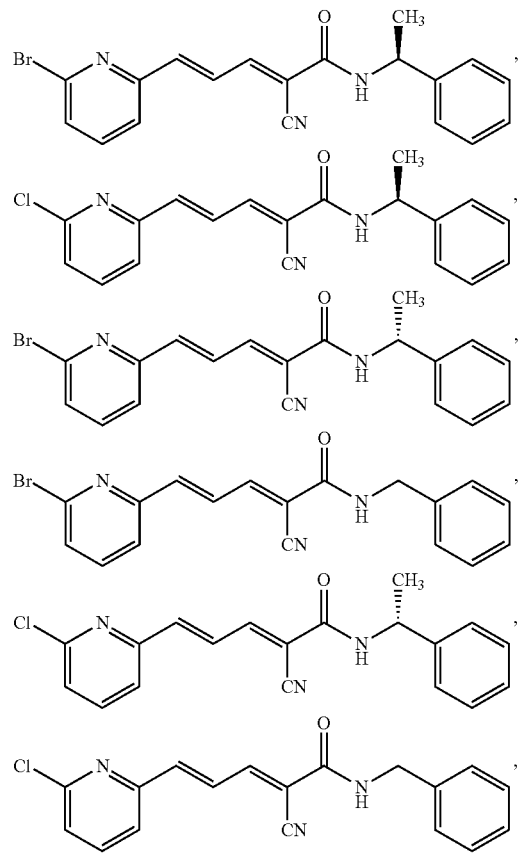

-continued

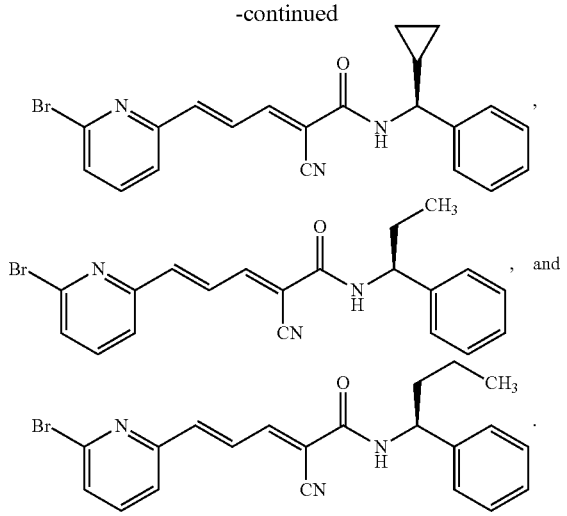

2. A compound having the structural formula:

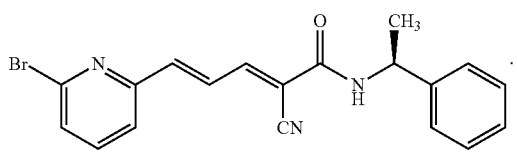

3. A compound having the structural formula:

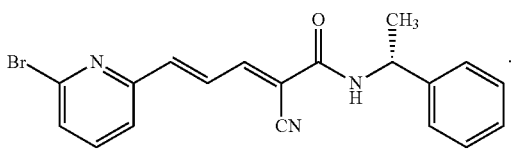

4. A pharmaceutical composition comprising a compound as recited in claim 2, together with a pharmaceutically acceptable carrier.

5. The pharmaceutical composition comprising as recited in claim 4, wherein said pharmaceutical composition is a topical pharmaceutical composition.

6. A pharmaceutical composition comprising a compound as recited in claim 1, together with a pharmaceutically acceptable carrier.

7. The pharmaceutical composition comprising as recited in claim 6, wherein said pharmaceutical composition is a topical pharmaceutical composition.

8. A pharmaceutical composition comprising a compound as recited in claim 3, together with a pharmaceutically acceptable carrier.

9. The pharmaceutical composition comprising as recited in claim 8, wherein said pharmaceutical composition is a topical pharmaceutical composition.

* * * * *